(12) United States Patent
Keller

(10) Patent No.: US 8,263,645 B2
(45) Date of Patent: Sep. 11, 2012

(54) DISODIUM CROMOGLYCATE COMPOSITIONS AND METHODS FOR ADMINISTERING SAME

(75) Inventor: Manfred Keller, Munich (DE)

(73) Assignee: PARI Pharma GmbH, Munich (DE)

( * ) Notice: Subject to any disclaimer, the term of this patent is extended or adjusted under 35 U.S.C. 154(b) by 1220 days.

(21) Appl. No.: 11/671,330

(22) Filed: Feb. 5, 2007

(65) Prior Publication Data
US 2007/0193577 A1 Aug. 23, 2007

Related U.S. Application Data

(60) Provisional application No. 60/867,680, filed on Nov. 29, 2006, provisional application No. 60/764,763, filed on Feb. 3, 2006.

(51) Int. Cl.
*A61K 31/35* (2006.01)
*A61K 31/335* (2006.01)
*A61K 31/352* (2006.01)

(52) U.S. Cl. .......................... 514/456; 514/449; 514/453

(58) Field of Classification Search .................. 514/449, 514/453, 456
See application file for complete search history.

(56) References Cited

U.S. PATENT DOCUMENTS

| 4,192,860 | A * | 3/1980 | Griffiths | 424/43 |
| 6,792,939 | B1 * | 9/2004 | Weinstein | 128/200.19 |
| 7,029,656 | B2 * | 4/2006 | Coifman | 424/43 |
| 2003/0124063 | A1 * | 7/2003 | Chaudry et al. | 424/46 |
| 2006/0062737 | A1 * | 3/2006 | Hofmann et al. | 424/45 |
| 2007/0036860 | A1 * | 2/2007 | Wigmore | 424/471 |
| 2007/0071686 | A1 * | 3/2007 | Lintz et al. | 424/45 |

FOREIGN PATENT DOCUMENTS
WO   WO 2005/037256   *   4/2005

OTHER PUBLICATIONS

McGraw-Hill Encyclopedia of Science & Technology, 9th edition, McGraw-Hill: New York, 2002 pp. 303.*
MacMillan Encyclopedia of Physics, J. S. Rigden, ed., vol. 4, Simon & Schuster Macmillan: New York, 1996, pp. 1677.*
Bernstein, I. L., "Cromolyn Sodium," Chest, 1985, 87, pp. 68S-73S.*
Lacy, C.; Armstrong, L. L.; Lipsy, R. J.; Lance, L. L. Drug Information Handbook, Lexi-Comp, Inc.: Cleveland, 1993, pp. 232-233.*
Merck Manual of Medical Edition, Second Home edition article, entitled, "Lung Cancer"—accessed on Jul. 28, 2010 at www.merc.com/mmhe/print/sec04/ch057/ch057a.html.*
Muers, M. F. "Overview of nebuliser treatment," Thorax, 1997, 52(Suppl. 2), pp. S25-S30.*
Lange's Handbook of Chemistry, 9th Edition, Handbook Publishers, Inc.: Sandusky, Ohio, 1956, pp. 1651.*
Keller, et al., "Did Inappropriate Delivery Systems Hamper Therapeutic Efficacy of Di-Sodium-Cromo-Glycate (DSCG)? Time for Reappraisal", ISAM, Jun. 18-22, 2011, Rotterdam, The Netherlands, 1 page.
Moeller, et al., "Efficacy of an Isotonic Small Droplet Size Nebulized DSCG on Asthma Control in Children", European Respiratory Society Annual Congress, Oct. 4-8, 2008, Berlin, Germany, 1 page.
Stangl, et al., "Customizing an Electronic Nebulizer", ISAM 15th, Mar. 14-18, 2005, Perth, Australia, 1 page.

* cited by examiner

*Primary Examiner* — James H. Alstrum-Acevedo
(74) *Attorney, Agent, or Firm* — Edwards Wildman Palmer LLP

(57) ABSTRACT

Methods for the treatment of patients that are afflicted with pulmonary conditions, such as a pulmonary disease are described. The methods may involve the administration of aerosolized medicines. More specifically, compositions including disodium cromoglycate (DSCG) and therapeutic methods that include the pulmonary administration of such compositions are described.

58 Claims, 5 Drawing Sheets

| DSCG concentration in % / DSCG dose in mg/0.5 ml | 2 / 10 | | 3 / 15 | | 4 / 20 | | 5 / 25 | |
|---|---|---|---|---|---|---|---|---|
| Breathing pattern | Adult | 3 yrs | Adult | 3 yrs | Adult | 3 yrs | Adult | 3 years |
| RF<3.3μm [%] | 53.2 ±0.6 | 52.5 ±1.0 | 52.8 ± 0.7 | 52.6 ±1.1 | 52.8 ±0.6 | 53.4 ±1.4 | 53.6 ±1.6 | 54.8 ±0.6 |
| DD [%] | 61.7±0.9 | 59.1.0±1.6 | 61.4±1.9 | 59.8±1.7 | 62.5 ±2.5 | 60.1 ±2.5 | 63.3 ±2.8 | 61.7 ±3.7 |
| RD<3.3μm [%] | 32.8 | 31.0 | 35.1 | 32.4 | 33.0 | 34.2 | 33.9 | 33.8 |
| Nebulisation time [min] | 1.2 ±0.2 | 1.2 ±0.5 | 1.1 ±0.3 | 1.2 ±0.2 | 1.3 ±0.3 | 1.4 ±0.3 | 1.5 ±0.3 | 1.4 ±0.4 |

FIGURE 5

DISODIUM CROMOGLYCATE COMPOSITIONS AND METHODS FOR ADMINISTERING SAME

CROSS-REFERENCE TO RELATED APPLICATIONS

This application claims priority to and the benefit of U.S. Provisional Application Ser. No. 60/867,680, filed Nov. 29, 2006, and U.S. Provisional Application Ser. No. 60/764,763, filed Feb. 3, 2006, the disclosures of which are expressly incorporated herein by reference in their entirety.

BACKGROUND OF THE INVENTION

1. Field of the Invention

The invention relates to methods for the treatment of patients that are affected by a pulmonary disease. The methods typically involve the administration of aerosolized medicines. More specifically, the invention relates to compositions comprising disodium cromoglycate (DSCG) and therapeutic methods that include the pulmonary administration of such compositions.

2. Related Art

Asthma is a major cause of morbidity and mortality in the world and there is evidence that the prevalence has increased over the past 20 years, especially in children. Asthma is a chronic inflammatory disorder of the lung and often involves infiltration of the airway by inflammatory cells such as activated lymphocytes and eosinophils, denudation of the epithelium, deposition of collagen in the subbasement membrane area and mast cell degranulation. These inflammatory cells release chemical mediators resulting in altered airways physiology, swelling of the mucosa and submucosa, stripping of and damage to the epithelium, thickening of the basement membrane, excessive production of bronchial secretion and enlargement of the smooth muscle. It was observed in animal studies that the migration and activation of inflammatory cells is partly controlled by chemotactic agents, e.g. platelet activating factor (PAF) or leukotriene B4 (LTB4), and an increased expression of adhesion molecules with receptor-ligand systems to leukocytes on epithelium and on vascular endothelial cells supporting the migration of inflammatory cells into lung tissue.

In a biopsy-proven (airway smooth muscle) study without allergen challenge in 17 asthmatic patients, 13 patients with eosinophilic bronchitis and 11 normal subjects, a significant difference in submucosal eosinophil count, thickness of basement membrane and lamina reticularis in asthmatic patients and patients with eosinophilic bronchitis was observed compared to the control group, but no differences were observed in the asthma/bronchitis patients. Across the disease groups, the median number of tryptase-positive mast cells in the bundles of airway smooth muscle was significantly higher in asthma patients compared to bronchitis patients and normal subjects ($p<0.001$), thus raising an important inflammation process difference between eosinophilic bronchitis and asthma.

In a study in six mildly symptomatic asthmatics with biopsy evidence about 5 to about 6 hours after local allergen challenge, a significant increase in neutrophils, eosinophils, mast cells and CD3+ lymphocytes, but not for CD4+ or CD8+ lymphocyte counts. A significant increase of endothelial intercellular adhesion molecule type I and E-selectin was also observed. All subjects also developed a localized bronchoconstriction with a fall in forced expiratory volume in 1 second (FEV1) and decrease in metacholine provocation concentration necessary to reduce FEV1 by about 20%.

Several studies on lung tissue specimens from asthmatic patients have demonstrated that due to the larger surface area, more severe inflammatory and structural changes occur in the distal lung (airways less than about 2 mm in diameter) and lung parenchyma of asthmatic patients, which may have a significant effect on the pathogenesis and treatment of the disease. A significant inverse correlation ($p=0.0014$) could be found in 21 asthmatic patients between the percentage of predicted FEV1 and the CD4+ inflammatory cell density in alveolar tissue, which was not observed for proximal samples. It was observed in a clinical study using lung specimens from asthmatic and non-asthmatic subjects that based on the accumulation of T-cells and eosinophils, a similar but more severe inflammatory process is present in the peripheral airways compared with the central airways in patients with asthma. Another study revealed that cells expressing IL-5 mRNA were significantly elevated in airways below about 2 mm compared to larger airways. These findings suggest that an inhaler controller therapy of inflammatory processes in asthma may result in a sufficient deposition of the drug in the smaller airways that are less than about 2 mm in diameter.

While the asthma pathogenesis of adult and childhood asthma is the same, the adverse effects and treatment strategies in childhood asthma are different compared to consequences in adult asthma patients. Early diagnosis and consecutive therapy are crucial for the short and long-term prognosis of this disease. Airway inflammation is treated according to the early intervention strategy with inhaled corticosteroids. In order to avoid side effects, such as growth retardation, the lowest therapeutically effective dose should be administered to children. Current nebulizers and pressurized metered dose inhalers (pMDIs) with spacers have been primarily developed for adults and have been adapted but not designed for use in young children. Lung deposition in adults from currently available nebulizers and pMDI/spacers ranges from about 8% to about 45% of the nominal dose, whereas studies in young children have shown lung deposition of only about 0.67% to about 5.4% of the nominal dose. This finding may suggest that aerosol droplets delivered by these devices are too large for the nose throat passage in young children.

Among many parameters, three major physiological differences affect pulmonary drug administration and should be considered for effective treatment for children 12 months to 8 years of age: (1) airway diameters of young children are significantly smaller than those of adults and older children; (2) younger children primarily inhale through the nose. Thus, a tight fitting facemask is needed to deliver the drug to the lungs. Consequently, lung deposition is significantly lower when inhaling through the nose versus inhalation via the oral route; and (3) the respiratory breathing patterns of young children are different from older children and adults with respect to the tidal volume (TV)—for infants is in the range of about 50 ml to about 100 ml, and respiratory rates—for infants is about 30 breaths per minute. The inspiratory flow (infants: in the range of about 3.5/min to about 15/min) may be too low to keep up with the driving flow of many nebulizer compressor configurations, so most of the nebulizer output is wasted.

Due to its excellent safety profile, inhaled disodium cromoglycate (DSCG) is used mainly as a controller medication for asthma in children, but its use now in childhood asthma management is in steep decline. One of the earliest studies investigating the mechanism of action of DSCG showed that the drug inhibited the influx of calcium ions and phosphorylated a 78 kDa protein in rat mast cells. These findings were associated with an inhibition of histamine release following antigen challenge, thus proposing a mast cell stabilizing effect. An identical phosphorylation trough cyclic guanosine monophosphate (cGMP) caused by a reaction of DSCG was investigated. This study indicated that the 78 kDa protein may be a substrate for cGMP-related phosphorylation. In addition, a cross-tachyphylaxis between the inhibitory effects of DSCG and cGMP on histamine release from rat peritoneal mast cells has been found.

Yet another study described the existence of a small conductance chloride channel in rat peritoneal mast cells which may be activated by cGMP and high intracellular calcium leading to an influx of chloride ions, hyperpolarization of the mast cell membrane, calcium influx and finally causing mast cell degranulation associated with inflammatory mediator release. DSCG has been shown to block intermediate conductance chloride channels which were activated following immunological stimulation of mucosa-like mast cells and colonic carcinoma epithelial cells. Thus, by preventing chloride channel activation trough DSCG, inflammatory cells may maintain a normal resting physiological state and may prevent release of inflammatory mediators. The maintenance of the physiological state may also explain the excellent safety profile of DSCG.

DSCG is currently available in the form of compositions for oral, nasal, ophthalmic, and pulmonary administration. Within the group of products for pulmonary inhalation, the known formulations are designed for administration as pressurized metered-dose inhalers (pMDIs), dry powder inhalers (DPIs), and nebulized aerosols.

SUMMARY OF THE INVENTION

The invention satisfies the above needs by providing improved nebulized aerosols and compositions which may be aerosolized thereof. In contrast to conventional inhalation therapy with common DSCG formulations, it is possible according to the invention to deliver a large fraction of the drug substance used (e.g., of the amount of drug substance contained in the volume of the formulation which is filled into the reservoir of a nebulizer) to the patient's lungs where it can become effective. Furthermore, following the teachings of the invention, it may also be possible to effectively treat pediatric patients suffering from certain pulmonary diseases such as asthma.

In one aspect, the invention provides a method for the treatment of a patient afflicted with a pulmonary disease or condition. The method may include providing a volume of an aqueous composition including disodium cromoglycate (DSCG) in dissolved form by providing a nebulizer capable of nebulizing said composition into an aerosol exhibiting a fine particle fraction of at least about 30%, and nebulizing the volume by the nebulizer into an aerosol. In the context of this aspect of the invention, the fine particle fraction may be defined as the percentage by weight of aerosol droplets having a diameter of less than about 5 μm.

In an additional aspect, the patient may be a pediatric patient or an adult patient and may be afflicted with a pulmonary disease or condition such as chronic obstructive pulmonary disease, allergic asthma, non-allergic asthma, wheezing, and any other inflammatory or allergic lung diseases. Moreover, the aqueous composition may include other active compounds such as beta-agonists, anticholinergics, inhaled steroids, vasodilating drugs, or—anti-inflammatory drugs. The beta-agonist may be albuterol, terbutalin, procaterol, and formoterol, as a salt, isomer, ester, ether or prodrug thereof. The anticholinergic may be a compound such as ipratropium, oxitropium, and glycopyrrolate as a salt, ester, ether, isomer or prodrug thereof. The inhaled steroid may be a compound such as budesonide, ciclesonide, fluticasone, and mometasone as a salt, ester, ether, isomer, or prodrug thereof. The aqueous composition may also include excipients, salts, sugar, sugar alcohols, and sweeteners to improve the taste and acceptance by the patient.

In another aspect, the invention provides a nebulized aerosol which is adapted for pulmonary administration by oral or nasal inhalation, and which includes droplets of an aqueous solution of DSCG. The aerosol is further characterized in that it has a fine particle fraction of droplets having a size less than about 3.3 μm of at least about 30%, and wherein the difference between the mass median aerodynamic diameter when measured at room temperature and at a relative humidity of about 50% and the mass median aerodynamic diameter when measured at room temperature and at a relative humidity of about 95% is less than 0.5 μm. The fine particle fraction may be defined as the percentage by weight of aerosol droplets having a diameter of less than about 3.3 μm.

In a further aspect, the invention provides a nebulizer for exhibiting a residual volume of less than about 0.2 ml for nebulizing an aqueous composition having a concentration in the range of about 1 to about 5 wt-% disodium cromoglycate in dissolved form. The nebulized aerosol may exhibit a fine particle fraction in droplets having a size less than about 3.3 μm of at least about 30%. Specifically, the nebulizer is an electronic vibrating membrane nebulizer.

In a further aspect, particular formulations for practicing the invention may be aqueous compositions including in the range of about 5 to about 60 mg of DSCG per dose unit, and in particular in the range of about 5 mg to 50 mg, and more particularly, in the range of about 10 mg to about 40 mg. The volume of a dose unit may be from about 0.4 to about 2 ml, and specifically in the range of about 0.5 ml to about 1 ml. Additionally, the osmolality of the composition may be at least about 200 mOsmol/kg. Furthermore, the aqueous composition may exhibit a dynamic viscosity in the range of about 1 mPas to about 2 mPas, and in particular, a dynamic viscosity in the range of about 1 mPas to about 1.4 mPas. The aqueous composition may exhibit a surface tension in the range of about 50 mN/m to about 75 mN/m.

In one aspect, nebulizers for practicing the invention are nebulizers which may be capable of nebulizing a composition including in the range of about 5 mg to about 60 mg of DSCG dissolved in a unit dose volume into an aerosol exhibiting a fine particle fraction in droplets having a size less than about 3.3 μm of at least about 30%. In another aspect, the nebulizer may be a device that has a residual volume of less than about 0.2 ml. Moreover, the nebulizer may be adapted to emit the composition in the form of an aerosol whose droplets exhibit a mass median aerodynamic diameter (MMAD) of less than about 4 μm to enable that a therapeutic effective DSCG dose can be deposited into the lung periphery being regarded as target site to improve clinical efficacy over currently used DSCG inhalation products. In particular, the nebulizer may be capable of nebulizing the aqueous composition into an aerosol such that the droplets exhibit a mass median aerodynamic diameter having a geometric standard deviation of less than about 2.3, and more particularly, a mass median aerodynamic diameter having a geometric standard deviation of less than about 2.

In another aspect of the invention, the nebulizer may be capable of nebulizing the aqueous composition into an aerosol that may exhibit a fine particle fraction of at least about 30% in droplets having a size less than about 3.3 μm and where greater than about 20 wt.-% of the nominal drug dose may be contained in droplets having a size in the range of about 2 µm to about 4 µm. In a more particular aspect, the nebulizer may be capable of nebulizing the aqueous composition into an aerosol such that the droplets exhibit a mass median aerodynamic diameter of less than about 4 µm. The difference between the mass median aerodynamic diameter when measured at room temperature and at a relative humidity of about 50% and the mass median aerodynamic diameter when measured at room temperature and at a relative humidity of about 95% is less than about 0.5 µm.

In a further aspect, the nebulizer may be capable of emitting at least about 40 wt.-% of the volume of the aqueous composition in aerosol form. The nebulizer may exhibit a residual volume of less than about 0.2 ml and may be capable of nebulizing the volume of the aqueous composition in less than about 5 minutes. In particular, the nebulizer that may be employed in the methodology of the invention may be a jet nebulizer, an ultrasonic nebulizer, a vibrating membrane nebulizer, and an electronic nebulizer, for example.

According to an aspect of the invention, a nebulized aerosol adapted for pulmonary administration by oral or nasal inhalation or administration is provided. The aerosol may include droplets of an aqueous solution of disodium cromoglycate, where the aerosol may have a fine particle fraction of at least about 30% in droplets having a size less than about 3.3 µm. Moreover, the fine particle fraction may be defined as the percentage of aerosol droplets having a diameter of less than about 3.3 µm. Specifically, at least about 40% of the aerosol droplets have a diameter less than about 4 µm and the fine particle fraction may be at least about 30% in droplets having a size less than about 3.3 µm. Furthermore, the droplets may exhibit a mass median aerodynamic diameter of less than about 4 µm and may have a geometric standard deviation of less than about 2.3, and more specifically have a geometric standard less than about 2. Moreover, the effective amount of disodium cromoglycate may in the range of about 5 mg to about 50 mg and contained in a volume of less than about 2 ml.

In a further aspect, the aerosol may be generated by a nebulizer such as jet nebulizers, ultrasonic nebulizers, perforated and non perforated vibrating membrane nebulizers, and other electronic or mechanical nebulizers generating aerosols by means of other principles, such as electro-hydrodynamic-, or electrostatic- or capillary forces, or via condensation, high pressure jets and extrusion.

One aspect of the invention relates to a method for reaching target cells located in deep airways of a patient afflicted with a pulmonary disease or condition. The methodology may include providing a composition including an effective amount of disodium cromoglycate in dissolved form, and nebulizing the composition using a nebulizer to produce greater than about 20 wt.-% of the nominal drug dose in droplets having a size in the range of about 2 µm to about 4 µm such that the droplets reach the target cells in the lung periphery of the patient.

In another aspect, the nebulizer may be capable of producing greater than about 30 wt.-% of the nominal drug dose in droplets having a size less than about 3.3 µm. Specifically, the nebulizer may be capable of exhibiting a high fine droplet drug output/time defined as respirable drug delivery rate for droplets having a size less than about 3.3 µm, and more specifically, a respirable drug delivery rate of greater than about 4% of the nominal dose disodium cromoglycate/minute.

In a further aspect, the nebulizer may employ a composition volume of less than about 2 ml, and more specifically, a composition volume in the range of about 0.2 ml to about 1.5 ml. The disodium cromoglycate may have a concentration of greater than about 1 wt.-%, and more particularly, a concentration in the range of about 2 wt.-% to about 5 wt.-%.

In yet a further aspect, the nebulizer may be capable of aerosolizing a nominal dose of DSCG in the range of about 5 mg to about 50 mg in less than about 3 minutes having a respirable fraction less than about 4 µm of greater than about 40%. More particularly, the nebulizer may be capable of generating and delivering to the patient in less than about 3 minutes a respirable dose of at least 2 mg in droplets having a size less than about 3.3 µm and wherein more than about 20 wt.-% of the effective amount of disodium cromoglycate is contained in droplets having a size in the range of about 2 µm to about 3.3 µm. Furthermore, the nebulizer may be a low wastage perforated vibrating mesh nebulizer with a residual volume of less than about 0.5 ml following nebulization of the filled volume. The nebulizer may be capable of delivering a dose ex-mouthpiece deviating less than about 20% from a breathing pattern and wherein the delivered dose does not fall below about 50% when breathing patterns of children are applied.

Another aspect of the invention is a method for delivering an aerosolized composition to a patient. The method may include providing a nebulizer such that the nebulizer exhibits a residual volume of less than about 0.2 ml, and nebulizing an aqueous composition including an effective amount of dissolved disodium cromoglycate having a concentration in the range of about 1 wt.-% to about 5 wt.-% into an aerosol exhibiting a fine particle fraction of at least about 30% in droplets less than about 3.3 µm such that the aerosolized composition is delivered to the patient. In particular, the fine particle dose in droplets less than about 3.3 µm may be at least 2 mg where more than about 20 wt.-% of the effective amount of disodium cromoglycate may be contained in the droplets having a size in the range of about 2 µm to about 3.3 µm. Additionally, the dosing frequency may be in the range of about one time daily to about three times daily.

In a further aspect, a delivered dose greater than about 50% of a charged dose may be loaded into the nebulizer. The effective amount of disodium cromoglycate may be nebulized in less than about 5 minutes and the effective amount of disodium cromoglycate may be in the range of about 5 mg to about 50 mg.

In yet a further aspect, the nebulizer may be capable of delivering a dose ex-mouthpiece which deviates less than about 20% from the breathing pattern such that the delivered doses do not fall below about 50%, when breathing patterns of children are applied.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention claimed. The detailed description and the specific examples, however, indicate only preferred embodiments of the invention. Various changes and modifications within the spirit and scope of the invention will become apparent to those skilled in the art from this detailed description.

BRIEF DESCRIPTION OF THE FIGURES

The accompanying drawings, which are included to provide a further understanding of the invention, are incorporated in and constitute a part of this specification, illustrate embodiments of the invention and together with the detailed description serve to explain the principles of the invention.

No attempt is made to show structural details of the invention in more detail than may be necessary for a fundamental understanding of the invention and various ways in which it may be practiced.

FIG. 5 is a table showing data illustrating that the eFlow® 30S performs consistently over a wide range of disodium cromoglycate concentrations and nominal doses.

DETAILED DESCRIPTION OF THE INVENTION

Figure 1:
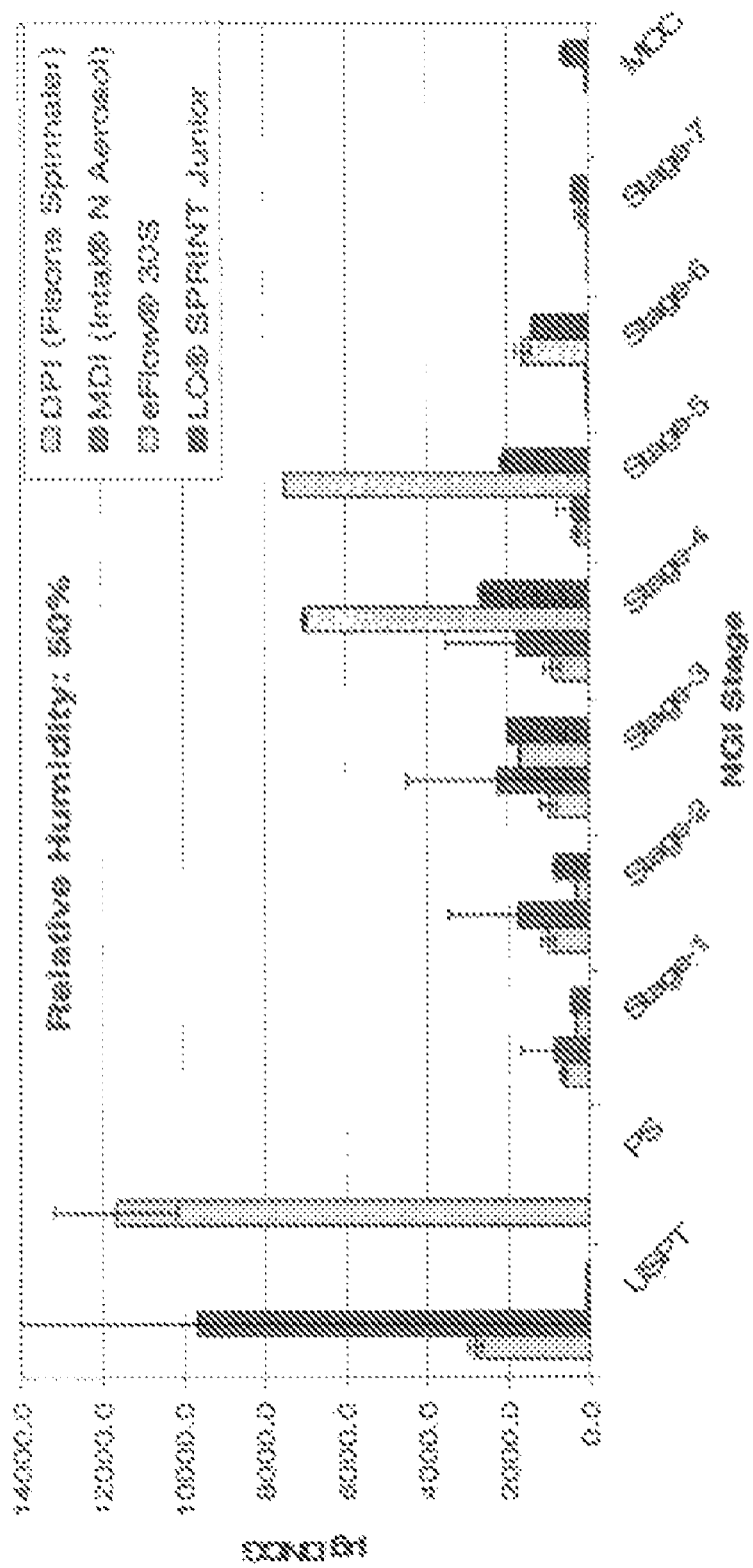
FIG. 1 shows the mean results on NGI drug distribution patterns in mg±SD obtained from about 20 mg DSCG, each aerosolized through 4 inhalation systems in triplicate, each at about 50% RH.

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. It also is be noted that as used herein and in the appended claims, the singular forms "a," "an," and "the" include the plural reference unless the context clearly dictates otherwise. This, for example, a reference to "a particle" is a reference to one or more particles and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein.

Any numerical values recited herein include all values from the lower value to the upper value in increments of one unit provided that there is a separation of at least two units between any lower value and any higher value. As an example, if it is stated that the concentration of a component or value of a process variable such as, for example, osmolality, temperature, pressure, time and the like, is, for example, from 1 to 90, specifically from 20 to 80, more specifically from 30 to 70, it is intended that values such as 15 to 85, 22 to 68, 43 to 51, 30 to 32 etc., are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Moreover, provided immediately below is a "Definition" section, where certain terms related to the invention are defined specifically. Particular methods, devices, and materials are described, although any methods and materials similar or equivalent to those described herein can be used in the practice or testing of the invention. All references referred to herein are incorporated by reference herein in their entirety. In particular, attached Appendices A, B, and C are herein incorporated by reference herein in their entirety.

DEFINITIONS

BTS British Thoracic Society
cGMP Cyclic guanosine monophosphate
COPD Chronic obstructive pulmonary disease
DDR Drug delivery rate
DSCG Disodium cromoglycate
DPI Dry powder inhaler
$FEV_1$ Forced expiratory volume in 1 second
GINA Global Initiative for Asthma
GRAS Generally regarded as safe
GSD Geometric standard deviation
$LTB_4$ Leukotriene $B_4$
MMAD Mass median aerodynamic diameter
MMD Mass median diameter
NGI Next generation impactor
MDI Metered dose inhaler
NAEPP National Asthma Education and Prevention Program
PAF Platelet activating factor
PEF Peak expiratory flow
pMDI Pressurized metered dose inhaler
RDDR Respirable drug delivery rate
RH Relative humidity
RF Respirable fraction
SAINT Sophia anatomical infant nose throat
SLD in vitro lung dose obtained in the SAINT model
VC Vital capacity
VMD Volumetric mass diameter Treatment, as used herein, refers to an intervention aimed at the prevention, management, control, or therapy, whether symptomatic, curative, or palliative, of any disease, symptom or condition that may affect a patient.

An aerosol, as used herein, is a system comprising a continuous gas phase and, dispersed therein, a discontinuous phase of liquid and/or solid particles.

Nebulization, as used herein, refers to the conversion of a liquid, such as a liquid solution, emulsion, or suspension, into an aerosol. Thus, a nebulized aerosol comprises liquid droplets dispersed in a continuous gas phase. The liquid droplet may optionally comprise solid particles which are suspended within the droplets.

A nebulizer, as used herein, is a device which is capable of converting a liquid material into a nebulized aerosol which is typically inhalable by a human via the nose or the mouth.

The residual volume of a nebulizer is the volume of liquid which cannot be aerosolized, but which remains in the reservoir of the device.

The fine particle fraction of an aerosol, as used herein, refers to the fraction of aerosol droplets having a diameter below a specified value, such as 5 μm.

The mass median aerodynamic diameter (MMAD), as used herein, describes that diameter which is surpassed by 50 wt.-% of all droplets of an aerosol. It may be determined by cascade impaction methods.

Pharmaceutically acceptable (or pharmacologically acceptable), as used herein, refers to excipients, compounds and compositions that are generally regarded as safe for human use, and which are typically accepted as safe by the major regulatory agencies such as the FDA.

Aqueous, as used herein, refers to a system or composition which comprises a liquid phase whose predominant liquid constituent is water. Thus, an aqueous composition may also comprise solutes or non-aqueous liquids to some extent.

"Nanocrystals" and "nanosuspensions" as used herein may be obtained by wet milling or high-pressure, homogenization processes. Typically, nanocrystals and nanosuspensions may include polymer or surfactant to coat the drug particles, thereby improving stability.

"Nanocapsules" as used herein, generally refer to solidified micellar systems, micro-emulsions or coated colloidal solid-drug systems, in which the drug is embodied in a polymer, such as ethylcellulose. They can be produced by spray drying a drug polymer solution, nanosuspension and water-in-oil emulsion, or by polymerization methods.

"Liposomes," as used herein may include small unilamellar vesicles, which have a size in the range of about 20 nm to about 50 nm, and large unilamellar or multilamellar vesicles, which have a size in the range of about equal to or less than about 1 μm. Liposomes are concentric vesicles and their shell is formed by one or several water insoluble phospholipid bilayers. The lipophilic parts of the phospholipids may be facing each other, whereas the hydrophilic parts may face towards the aqueous outer phase and nucleus. Hydrophilic drugs may be encapsulated in the aqueous nucleus and interstitium, whereas lipophilic drugs may be incorporated in the lipid layer of the phospholipid membranes. Liposomes may be suitable drug carriers as they can solubilize drug molecules, reduce the toxicity of a drug substance and improve cell permeation to target specific cells. Examples are the reduced nephrotoxicity of amphotericin B or cardiotoxicity of the cytostatic doxorubicin (Doxil®, Ortho Biotech. NJ, USA) on intravenous administration when liposomal formulations are used.

The invention is based on the discovery that the effectiveness of inhalation therapy with DSCG can be substantially improved by either using an aqueous composition of DSCG for nebulization which has properties that differ from those of the conventional DSCG formulations, or by selecting a nebulizer with characteristics that differ from those of the nebulizers that are used in conventional DSCG inhalation therapy, or by changing both the formulation and the nebulizer.

Accordingly, the invention provides methodologies for the treatment of a patient afflicted with a pulmonary disease or condition by providing a volume of an aqueous composition including in the range of about 10 to about 60 mg of disodium cromoglycate in solution, providing a nebulizer capable of nebulizing the composition into an aerosol exhibiting a fine particle fraction of at least about 30%; and nebulizing said volume by said nebulizer into an aerosol. In the context of this aspect of the invention, the fine particle fraction may be defined as the percentage by weight of aerosol droplets having a diameter of less than about 5 μm, and more particularly, a diameter less than about 3.3 μm.

The deposition of aerosolized drug in the lungs is determined by different factors, that is, patient and drug/device-related factors. The individual lung anatomy and the breathing maneuvers of the patient have a major impact on drug deposition. On the other hand, the design, function and quality of the device, as well as the interaction of drug formulation and device, play an important role. Crucial parameters are the delivery efficiency and consistency, particle size and aerosol plume velocity.

An inhalation system has to produce a particle size distribution suitable for delivery to the lungs. For inhaled delivery of medications, the fraction of respirable particles or droplets (percentage of particle mass in the range of about 1 μm to about 5 μm in diameter) should be maximized. Particles in this size range will be deposited primarily by sedimentation in the peripheral lung regions, the bronchioles and alveoli. Sedimentation is the major mechanism of deposition in the therapeutic use of aerosols. Although about 3 to about 5 μm particles are ideal for topical applications, particles in the range of about 1 to about 3 μm are needed for systemic administration of drugs via the lungs, such as insulin, hormones and opioids. Inertial impaction associated with larger particles (diameter greater than about 5 μm) should be minimized to avoid undesired oropharyngeal deposition.

There are two widely known classes of medical nebulizers: the jet nebulizer, which is powered by compressed air, and the ultrasonic nebulizer, which derives the energy required to aerosolize drugs from high frequency sound waves. Jet nebulizers are driven either by a portable compressor or from a central air supply.

Essentially, a high-speed air flow through a narrow, nozzle orifice entrains and disperses the liquid into droplets (primary generation) via a viscosity-induced instability. Droplet dispersion is improved by impaction on a baffle structure adjacent to the nozzle orifice transferring kinetic energy further into increased droplet surface area (secondary generation). The resulting droplet size distribution still contains only a small fraction of respirable aerosol (droplets in the range of about 5 to about 6 μm in size) and the large droplets are recirculated within the nebulizer by means of secondary impaction structures. This process is associated with evaporation effects that cause the gas phase to be nearly saturated with vapor, as well as a temperature, decrease within the nebulizer. A considerable part of the vapor arises from the larger recirculating droplets, thus increasing drug concentration in the remaining liquid.

The aqueous composition may be provided in a specific volume and includes in the range of about 5 to about 60 mg of the drug substance. Specifically, the specific volume may be in the range of about 5 mg to about 60 mg, and more specifically, may be in the range of about 10 mg to about 60 mg. The volume, which may also be referred to as the volume of a dose, or a dose unit volume, or a unit dose volume, is the volume which is intended for being used for one single administration. Specifically, the volume may be in the range from about 0.4 to about 2 ml. Particularly useful for carrying out the invention is a volume in the range from about 0.5 to about 1.5 ml, or a volume in the range from about 0.5 to about 1.0 ml, especially in combination with the selection of a nebulizer that exhibits only a small residual volume, such as less than 1 ml, or less than 0.5 ml, and most preferably less than 0.2 ml.

In another specific embodiment, the dose of the drug substance, DSCG, which is dissolved in the volume may be in the range from about 5 to about 50 mg, or in the range from about 10 to about 40 mg, and particularly in the range from about 10 to 20 mg. The effective dose of DSCG may also depend upon its specifically intended use and may be determined without undue experimentation by one of skill in the art, e.g. in consideration of the nebulizer to be used or the type of patient that is to be treated. For example, the delivered dose ex mouthpiece may be greater than about 30%, and more specifically about 50% of the nominal dose based on a breathing pattern including a tidal volume in the range of about 50 ml to about 750 ml and in the range of about 10 breaths/minute to about 50 60?? breaths/minute. This wide range may be due to the different breathing profile across different ages and patients severity status. The inhalation of the liquid medication by spontaneous breathing may be accomplished by applying in the range of about 5 spontaneous inhalations to about 60 spontaneous inhalations, and more particularly, in the range of about 10 spontaneous inhalations to about 30 spontaneous inhalations translating into inhalation times of about 0.5 minutes to about 5 minutes. It is also known that uniformity of lung delivery can be improved when several and not only 1-2 breaths as common for pMDIs and DPIs are applied. This is particularly important for children who lack the ability to co-ordinate puffing and breathing upon inhalation.

Moreover, the dose and the volume may be selected to result in a concentration of the dissolved DSCG in the range from about 1 to about 5% by weight. In one particular embodiment, the concentration is about 1 wt.-%, about 2 wt.-%, about 4 wt.-%, or about 5 wt.-%, respectively. For example, the method may be conducted with about 2 ml of a composition including about 20 mg of DSCG, or with about 1 ml of a composition including about 20 mg of DSCG, or with about 0.5 ml of a composition including about 25 mg, and so forth. The selection of a relatively high concentration (or of a relatively low volume) for a given dose of DSCG is advantageous in that it would potentially reduce the inhalation time; on the other hand, the effect of the residual volume of almost any nebulizer is that a decrease in the unit dose volume will also decrease the fraction of the drug substance which is actually emitted in aerosolized form. According to the invention, however, it is possible to reduce the volume substantially if an appropriate nebulizer is selected which has a very low residual volume, such as less than about 0.5 ml, or even less than about 0.2 ml. An example of such nebulizer is the PARI eFlow series.

The aerosol may be adapted for pulmonary administration by oral or nasal administration. This means that it fulfills the standard requirements for formulations intended for these routes of administration as found in the current pharmacopeias or guidance documents issued by regulatory bodies such as the U.S. Food and Drug Administration (FDA).

According to another embodiment, the aqueous composition has a pH in the range of about pH 4 to about pH 8, in particular from about pH 5 to pH 7.5. The pH may be adjusted by the addition of a solution containing an acidic salt or an acid (e.g., hydrochloric or sulfuric acid); or of a basic salt or a base (e.g., sodium hydroxide). In case of insufficient stability of the formulation, aqueous buffered systems (citrate, acetate, phosphate) may be added to keep the pH within a physiologically acceptable range. A variety of buffers known in the art may be used in the formulation of the invention, such as various salts of organic or inorganic acids, bases, or amino acids, and including various forms of citrate, phosphate, tartrate, succinate, adipate, maleate, lactate, acetate, bicarbonate, or carbonate ions.

If a drug is molecularly dissolved it can be classified as a real solution, whereas colloidal solutions consist of homogeneously dispersed drug particles in a colloidal size range (less than about 100 nm). The four dispersed systems applicable as inhalation formulations may require excipients, such as surfactants, lecithin, phospholipids or polymers, to facilitate the solubization process. Phospholipids, which are contained in lecithin of plant or animal origin, are very popular due to their occurrence in cell membranes.

As an example, a novel micellar solution or budesonide has been developed (PARI GmbH, Germany) consisting of micelles in a size range of about 10 nm to about 25 nm, confirmed by photon correlation spectroscopy. Solubilization was achieved by an amphiphilic surfactant with a high hydrophilic-lipophilic balance value, lecithin and/or phospholipids mixture blended in a distinct ratio. As similar excipients have been used as contained in a commercially available artificial lung surfactant (Exosurf®, GlaxoSmithKline), toxicological safety can be expected. Exosurf has been used for the treatment of both adult and childhood respiratory distress syndrome. Lipophilic and water insoluble drugs, such as cyclosporin A and fluticasone-propionate can also be solubilized by this novel formulation technology.

The progress in drug delivery, with respect to other dosage forms (oral, parenteral), has stimulated the development of new aqueous inhalation drug products utilizing more sophisticated pharmaceutical technologies. Process technologies used for the manufacture of particulate systems in the nanosize range (less than about 200 nm) are of particular interest for nebulizer applications, which may include nanocrystals, nanocapsules, and liposomes, for example.

In a further embodiment, the aqueous composition exhibits an osmolality of at least about 200 mOsmol/kg. It has been found that the physiological tolerability may be improved significantly if DSCG is not administered in the form of a strongly hypotonic formulation, which is commonly done in prior art. More specifically, the osmolality may be in the range from about 200 to about 500 mOsmol/kg, or in the range from about 200 to about 400 mOsmol/kg, respectively. In a further embodiment, the aqueous composition may be isotonic or substantially isotonic, which means that its osmolality does not deviate much from that of physiological fluids, and typically refers to an osmolality in the range from about 300 mOsmol/kg.

The osmolality may be adjusted by the addition of osmotically active excipients, such as sodium chloride, magnesium chloride or sulfate, calcium chloride or sugars (e.g. glucose, lactose, sucrose, trehalose) or sugar alcohols (e.g. mannitol, xylitol, isomaltol) or cyclodextrins (e.g. beta-cyclodextrin, hydroxypropyl-beta-cyclodextrin, gamma-cyclodextrin, including Captisol).

To ensure efficient nebulization and appropriate aerosol characteristics, the aqueous composition may exhibit a dynamic viscosity of less than about 2 mPas, such as in the range from about 1 to about 2 mPas. Specifically, a dynamic viscosity in the range from about 1 to about 1.7 mPas, and especially in the range from about 1 to about 1.4 mPas may be used.

Another factor which may affect the quality of an aerosol generated by nebulization is the surface tension of the liquid composition which is nebulized. According to the invention, the surface tension should be at least about 30 mN/m, such as in the range from about 30 to about 75 mN/m, and in particular in the range from about 50 to about 75 mN/m.

Adjustments to the formulation by adjusting constituents of the formulations and their relative concentrations, including the amounts of DSCG may be made as needed according to the needs of the formulator, administrator or patient. Additional constituent elements of the multi-dose formulations of the invention may include water, a buffer, a pH-adjusting agent, a surfactant or anti-adsorbent, a wetting agent, a gelling agent, a drying agent, an osmolality adjusting agent, or virtually any other additive or carrier, depending upon the desired dosage form.

Additionally, polymeric excipients may be useful in the formulations of the invention, for among other things, to obtain slow release profile of the drug, such as chitosan,—or hydroymethylcellulose, hydroxyethylstarch, dextrans, and polyvinylpyrrolidon (Kollidon). Specifically, by obtaining a slow release profile of the drug would reduce the inhalation frequency to once or twice daily.

It may also be advantageous to employ surfactants in the isotonic DSCG formulations of the invention. Surfactants or anti-adsorbents that prove useful include polyoxyethylenesorbitans, polyoxyethylenesorbitan monolaurate, polysorbate-20, such as Tween-20™, polysorbate-80, and genapol, vitamin E-TPGS and lecithins or lecithin constituents.

For a potential reduction of drug adhesion or adsorption and solubilization of combination drugs and better lubrication, the composition may optionally further contain surfactants regarded as generally regarded as safe (GRAS) for inhalation, such as polysorbates, vitamin-TPGS and lecithins.

Another embodiment of the invention relates to the selection of the nebulizer which is used for aerosolizing the aqueous composition. According to the invention, a nebulizer should be selected which is capable of nebulizing the above-described composition into an aerosol having a fine particle fraction of at least about 30%. In this context, the fine particle fraction is that percentage by weight of aerosol droplets which have a diameter, or aerodynamic diameter, of less than 5 µm, and specifically less than about 3.3 µm. This fine particle fraction (FPF) may also be referred to as the respirable fraction of the aerosol. In further embodiments, the FPF may be at least about 40%, or at least about 50%, or at least about 60%, or at least about 70%, respectively.

Most notable, the fine particle fraction is typically very low in conventional DSCG inhalation therapy. For example, the inventors have determined the fine particle fractions as defined herein for the commercially available DSCG dry powder inhalers and pressurized metered-dose inhalers to be substantially below about 20%, which may explain their relatively poor effectiveness: the drug does not reach its target tissue to a sufficient degree. Even in nebulization, some of the most frequently used nebulizers generate aerosols having fine particle fractions of less than 20%.

Among jet nebulizers which meet the criteria for carrying out the invention include, for example, high-performance devices such as the PARI LC or PARI LC SPRINT, driven by an appropriate compressor such as the PARI Boy N (=PRONEB ultra in the USA). In particular, a nebulizer which also achieves a very high FPF such as an electronic perforated vibrating membrane nebulizer, and may include member of the PARI eFlow series. Other optional nebulizers may include ultrasonic nebulizers, electrohydrodynamic nebulizers, non vibrating or nonperforated membrane nebulizers, or nebulizers combining two or more of these types.

According to a further embodiment, a nebulizer may be selected which is capable of nebulizing the aqueous composition into an aerosol whose droplets exhibit a mass median aerodynamic diameter of less than about 4 µm. In other embodiments, the selected nebulizer may be capable of emitting the composition in aerosol form, where the mass median aerodynamic diameter of the aerosol droplets is less than about 3.8 µm, or less than about 3.6 µm, or less than about 3.5 µm, or less than about 3.4 µm, or less than about 3.3 µm, for example, or in the range from about 1 to about 4 µm, or from about 2 to about 3.5 µm.

Specifically, the geometric standard deviation of the mass median aerodynamic diameter of the selected nebulizer may be less than about 2.6, in particular less than about 2.5, or less than about 2.4, such as in the range from about 1.2 to about 2.4, or in the range from about 1.4 to about 2.3.

The mass median aerodynamic diameter (MMAD) and its geometric standard deviation (GSD) may be determined at room temperature and at relative humidity of about 50%. The values mentioned above refer to these conditions. However, the experimental determination may also be conducted at higher relative humidity, which may be a more realistic setup for certain in-vivo-applications. It has been found that certain aerosols are very sensitive in a humid environment. The phenomenon is particularly pronounced for hygroscopic drugs when administered with certain dry powder inhalers and pressurized metered-dose inhalers, including those currently used in DSCG therapy (e.g. Intal), where the mass median aerodynamic diameter is significantly higher at conditions of higher humidity. It has surprisingly been found by the inventors, however, that certain nebulizers are capable of aerosolizing the DSCG composition described above in a very robust fashion, and relatively independent of the relative humidity. In particular, it is preferred that a nebulizer is selected which is not only capable of generating an aerosol having a mass median aerodynamic diameter of less than about 4 µm (or less than 3.8 µm, 3.6 µm etc.), but which is also capable of doing so at high humidity conditions. In particular, the selection of a nebulizer is preferred where the difference between the mass median aerodynamic diameter when measured at room temperature and at a relative humidity of about 50% and the mass median aerodynamic diameter when measured at room temperature and at a relative humidity of about 95% is less than about 0.5 µm.

As already mentioned above, another very useful criterion for the selection of the nebulizer to carry out the invention is that its residual volume is particularly low, such as not more than about 1 ml. More particularly, the residual volume is less than about 0.5 ml, less than about 0.3 ml, and less than about 0.2 ml. An electronic nebulizer selected from the PARI eFlow series, such as the eFlow 30S, which has an extremely low residual volume of substantially less than 0.2 ml may be used.

Similarly, the nebulizer should be capable of emitting the major part, such as at least about 75%, or at least about 80%, respectively, of the aqueous DSCG composition in aerosolized form. In any case, a specific nebulizer for even the smallest volumes may be selected from the PARI eFlow series, which, due to its small residual volume, is capable of emitting substantially more than 75% of practically any variant of the aqueous DSCG composition disclosed herein.

Following the teachings of the invention, it is possible to achieve short and convenient inhalation times. The selected nebulizer may be capable of nebulizing the unit volume of the composition which includes a single dose of DSCG within a period of less than about 5 minutes. In further embodiments, the nebulization time is less than about 4 minutes, or less than about 3 minutes, or less than about 2 minutes, respectively.

The method of the invention is useful for the treatment of patients affected by a pulmonary disease or condition, such as chronic obstructive pulmonary disease, allergic asthma, non-allergic asthma, wheezing, and inflammatory lung diseases. A particular embodiment of the invention relates to the treatment of allergic asthma and chronic obstructive pulmonary disease. The method is very suitable also for those patients who find it difficult to operate a pressurized metered-dose inhaler or a dry powder inhaler, which is often the case with children or elderly. As the method of the invention provides a highly effective aerosol therapy based on small particle sizes, it is particularly suitable for pediatric patients in whom a significant lung deposition is only achieved with very small aerosol droplets, such as with aerosols having a mass median aerodynamic diameter of less than about 3.5 µm. To further improve the method when treating pediatric patients, it may be useful to equip the selected nebulizer with an appropriate facial mask, such as the Smartmask Kids in combination with an eFlow 25S nebulizer, which is a particularly preferred device combination for children of less than 5 years of age.

The method may further include the administration of a drug substance other than DSCG, or a suitable pharmaceutical composition thereof. Optionally, such further drug substance may be administered separately, or it may be incorporated in the DSCG composition described herein. The further drug substance may enhance the therapeutic efficacy by an additive or synergistic effect such as leucotriene antagonists, steroidal and non steroidal anti-inflammatory drugs, anti-allergics, β-agonists, anticolinergics, corticosteroids, testosterone derivatives, phosphodiesterase inhibitors, endothelin antagonists, mucolytics, antibiotics, antifungals, antivirals, antioxidants, vitamins, heparinoids, α-antitrypsin, and lung surfactants, for example.

Among the active compounds which may be useful are, for example, substances selected from the groups of anti-inflammatory compounds, anti-allergics, glucocorticoids, anti-infective agents, antibiotics, antifungals, antivirals, mucolytics, antiseptics, vasoconstrictors, wound healing agents, local anaesthetics, peptides, and proteins.

Examples of potentially useful anti-inflammatory compounds are glucocorticoids and non-steroidal anti-inflammatory agents such as betamethasone, beclomethasone, budesonide, ciclesonide, dexamethasone, desoxymethasone, fluoconolone acetonide, flucinonide, flunisolide, fluticasone, icomethasone, rofleponide, triamcinolone acetonide, fluocortin butyl, hydrocortisone, hydroxycortisone-17-butyrate, prednicarbate, 6-methylprednisolone aceponate, mometasone furoate, elastane-, prostaglandin-, leukotriene, bradykinin-antagonists, non-steroidal anti-inflammatory drugs (NSAIDs), such as ibuprofen, indometacin, including any pharmaceutically acceptable salts, esters, isomers, stereoisomers, diastereomers, epimers, solvates or other hydrates, prodrugs, derivatives, or any other chemical or physical forms of active compounds comprising the respective active moieties.

Examples of potentially useful anti-allergic agents include the aforementioned glucocorticoids, and nedocromil, cetirizine, loratidine, montelukast, roflumilast, ziluton, omalizumab, heparins and heparinoids and other antihistamines, azelastine, cetirizine, desloratadine, ebastine, fexofenadine, levocetirizine, loratadine.

Examples of anti-infective agents, whose class or therapeutic category is herein understood as comprising compounds which are effective against bacterial, fungal, and viral infections, i.e. encompassing the classes of antimicrobials, antibiotics, antifungals, antiseptics, and antivirals, are -penicillins, including benzylpenicillins (penicillin-G-sodium, clemizone penicillin, benzathine penicillin G), phenoxypenicillins (penicillin V, propicillin), aminobenzylpenicillins (ampicillin, amoxycillin, bacampicillin), acylaminopenicillins (azlocillin, mezlocillin, piperacillin, apalcillin), carboxypenicillins (carbenicillin, ticarcillin, temocillin), isoxazolyl penicillins (oxacillin, cloxacillin, dicloxacillin, flucloxacillin), and amidine penicillins (mecillinam); cephalosporins, including cefazolins (cefazolin, cefazedone); cefuroximes (cefuroxime, cefamandole, cefotiam), cefoxitins (cefoxitin, cefotetan, latamoxef, flomoxef), cefotaximes (cefotaxime, ceftriaxone, ceftizoxime, cefinenoxime), ceftazidimes (ceftazidime, cefpirome, cefepime), cefalexins (cefalexin, cefaclor, cefadroxil, cefradine, loracarbef, cefprozil), and cefiximes (cefixime, cefpodoxim proxetile, cefuroxime axetil, cefetamet pivoxil, cefotiam hexetil), loracarbef, cefepim, clavulanic acid/amoxicillin, ceftobiprole; synergists, including beta-lactamase inhibitors, such as clavulanic acid, sulbactam, and tazobactam; carbapenems, including imipenem, cilastin, meropenem, doripenem, tebipenem, ertapenem, ritipenam, and biapenem; monobactams, including aztreonam; aminoglycosides, such as apramycin, gentamicin, amikacin, isepamicin, arbekacin, tobramycin, netilmicin, spectinomycin, streptomycin, capreomycin, neomycin, paromoycin, and kanamycin; macrolides, including erythromycin, clarythromycin, roxithromycin, azithromycin, dithromycin, josamycin, spiramycin and telithromycin; gyrase inhibitors or fluoroquinolones, including ciprofloxacin, gatifloxacin, norfloxacin, ofloxacin, levofloxacin, perfloxacin, lomefloxacin, fleroxacin, garenoxacin, clinafloxacin, sitafloxacin, prulifloxacin, olamufloxacin, caderofloxacin, gemifloxacin, balofloxacin, trovafloxacin, and moxifloxacin; tetracyclins, including tetracyclin, oxytetracyclin, rolitetracyclin, minocyclin, doxycycline, tigecycline and aminocycline; glycopeptides, including vancomycin, teicoplanin, ristocetin, avoparcin, oritavancin, ramoplanin, and peptide 4; polypeptides, including plectasin, dalbavancin, daptomycin, oritavancin, ramoplanin, dalbavancin, telavancin, bacitracin, tyrothricin, neomycin, kanamycin, mupirocin, paromomycin, polymyxin B and colistin; sulfonamides, including sulfadiazine, sulfamethoxazole, sulfalene, co-trimoxazole, co-trimetrol, co-trimoxazine, and co-tetraxazine; azoles, including clotrimazole, oxiconazole, miconazole, ketoconazole, itraconazole, fluconazole, metronidazole, tinidazole, bifonazole, ravuconazole, posaconazole, voriconazole, and ornidazole and other antifungals including flucytosin, griseofluvin, tonoftal, naftifine, terbinafine, amorolfine, ciclopiroxolamin, echinocandins, such as micafungin, caspofungin, anidulafungin; nitrofurans, including nitrofurantoin and nitrofuranzone; -polyenes, including amphotericin B, natamycin, nystatin, flucocytosine; other antibiotics, including tithromycin, lincomycin, clindamycin, oxazolidinones (linezolids), ranbezolid, streptogramine A+B, pristinamycin A+B, virginiamycin A+B, dalfopristin/quinupristin (Synercid), chloramphenicol, ethambutol, pyrazinamide, terizidon, dapson, prothionamide, fosfomycin, fucidinic acid, rifampicine, isoniazid, cycloserine, terizidone, ansamycin, lysostaphin, iclaprim, mirocin B17, clerocidin, filgrastim, and pentamidine; antivirals, including aciclovir, ganciclovir, birivudine, valaciclovir, zidovudine, didanosine, thiacytidin, stavudine, lamivudine, zalcitabine, ribavirin, nevirapirine, delaviridine, trifluridine, ritonavir, saquinavir, indinavir, foscarnet, amantadine, podophyllotoxin, vidarabine, tromantadine, and proteinase inhibitors; plant extracts or ingredients, such as plant extracts from chamomile, hamamelis, echinacea, calendula, papain, pelargonium, essential oils, myrtol, pinen, limonen, cineole, thymol, mentol, tee tree oil, alpha-hederin, bisabolol, lycopodin, vitapherole; wound healing compounds including dexpantenol, allantoin, vitamins, hyaluronic acid, alpha-antitrypsin, anorganic and organic zinc salts/compounds, interferones (alpha, beta, gamma), tumor necrosis factors, cytokines, interleukins.

Examples of potentially useful mucolytics are DNase, P2Y2-agonists (denufosol), heparinoids, guaifenesin, acetylcysteine, carbocysteine, ambroxol, bromhexine, lecithins, myrtol, and recombinant surfactant proteins.

Examples of potentially useful local anaesthetic agents include benzocaine, tetracaine, procaine, lidocaine and bupivacaine.

Examples of potentially useful anti-allergic agents include the aforementioned glucocorticoids, and nedocromil. Examples of potentially useful peptides and proteins include antibodies against toxins produced by microorganisms, antimicrobial peptides such as cecropins, defensins, thionins, and cathelicidins.

For any of these and other explicitly mentioned examples of drug substances which are potentially useful for carrying out the invention, the compound names given herein should be understood as also referring to any pharmaceutically acceptable salts, solvates or other hydrates, prodrugs, isomers, or any other chemical or physical forms of the respective compounds comprising the respective active moieties.

Additionally drugs to treat pulmonary hypertension, such as prostacycline analogs, iloprost, remodulin, aviptadil, phosphodiesterase inhibitors, such as sildenafil, vardenafil, tadalafil, endothelian receptor antagonists, such as bosentane, virustatics, including podophyllotoxine, vidarabine, tromantadine, zidovudine; ribavirin, may be added.

Also, immunomodulators including methotrexate, azathioprine, cyclosporine A, tacrolimus, sirolimus, rapamycin, mycophenolate, mofetil, cytostatics and metastasis inhibitors, alkylants, such as nimustine, melphanlane, carmustine, lomustine, cyclophosphamide, ifosfamide, trofosfamide, chlorambucil, busulfane, treosulfane, prednimustine, thiotepa; antimetabolites, e.g. cytarabine, fluorouracil, methotrexate, mercaptopurine, tioguanine; alkaloids, such as vinblastine, vincristine, vindesine; antibiotics, such as alcarubicine, bleomycine, dactinomycine, daunorubicine, doxorubicine, epirubicine, idarubicine, mitomycine, plicamycine; complexes of secondary group elements (e.g. Ti, Zr, V, Nb, Ta, Mo, W, Pt) such as carboplatinum, cis-platinum and metallocene compounds such as titanocendichloride; amsacrine, dacarbazine, estramustine, etoposide, beraprost, hydroxycarbamide, mitoxanthrone, procarbazine, temiposide; paclitaxel, iressa, zactima, poly-ADP-ribose-polymerase (PRAP) enzyme inhibitors, banoxantrone, gemcitabine, pemetrexed, bevacizumab, ranibizumab may be added.

In a further embodiment other compounds may be used in combination with DSCG such as, proteinase inhibitors, such as alpha-anti-trypsin; antioxidants, such as tocopherols, glutathion; pituitary hormones, hypothalamic hormones, regulatory peptides and their inhibiting agents, corticotropine, tetracosactide, choriogonandotropine, urofolitropine, urogonadotropine, somatotropine, metergoline, desmopressine, oxytocine, argipressine, ornipressine, leuproreline, triptoreline, gonadoreline, busereline, nafareline, goselerine, somatostatine; parathyroid gland hormones, calcium metabolism regulators, dihydrotachysterole, calcitonine, clodronic acid, etidronic acid; thyroid gland therapeutics; sex hormones and their inhibiting agents, anabolics, androgens, estrogens, gestagenes, antiestrogenes; anti-migraine drugs, such as proxibarbal, lisuride, methysergide, dihydroergotamine, ergotamine, clonidine, pizotifene; hypnotics, sedatives, benzodiazepines, barbiturates, cyclopyrrolones, imidazopyridines, antiepileptics, zolpidem, barbiturates, phenyloin, primidone, mesuximide, ethosuximide, sultiam, carbamazepin, valproic acid, vigabatrine; antiparkinson drugs, such as levodopa, carbidopa, benserazide, selegiline, bromocriptine, amantadine, tiapride; antiemetics, such as thiethylperazine, bromopride, domperidone, granisetrone, ondasetrone, tropisetrone, pyridoxine; analgesics, such as buprenorphine, fentanyl, morphine, codeine, hydromorphone, methadone; fenpipramide, fentanyl, piritramide, pentazocine, buprenorphine, nalbuphine, tilidine; drugs for narcosis, such as N-methylated barbiturates, thiobarbiturates, ketamine, etomidate, propofol, benzodiazepines, droperidol, haloperidol, alfentanyl, sulfentanyl; antirheumatism drugs including tumor necrosis factor-alfa, nonsteroidal antiinflammatory drugs; antidiabetic drugs, such as insulin, sulfonylurea derivatives, biguanids, glitizols, glucagon, diazoxid; cytokines, such as interleukines, interferones, tumor necrosis factor (TNF), colony stimulating factors (GM-CSF, G-CSF, M-CSF); proteins, e.g. epoetine, and peptides, e.g. parathyrin, somatomedin C; heparine, heparinoids, urokinases, streptokinases, ATP-ase, prostacycline, sexual stimulants, or genetic material.

In a further embodiment, the aqueous composition of the invention may also include other additives, excipients, sugar, sugar alcohols, flavors, salts, and sweeteners. Examples of the sugars include such sugars as glucose, fructose, lactose, sucrose, maltose, and isomaltose, and sugar alcohols such as sorbitol, maltitol, palatinit, and hydrogenated starch syrup. Examples of suitable sweeteners include natural sweeteners such as brazzeine, curculin, erythritol, fructose, glycyrrhizin, glycerol, hydrogenated starch hydrolysates, isomalt, lactitol, mabinlin, maltitol, mannitol, miraculin, monellin, pentadin, sorbitol, stevia, tagatose, thaumatin, and xylitol. Additionally, examples of suitable sweeteners also include artificial sweeteners such as acesulfame potassium, -alitame, aspartame, cyclamate, dulcin, neohesperidine dihydrochalcone, -neotame, P-4000, saccharin; and sucralose.

In yet a further embodiment, the invention provides a nebulized aerosol which is adapted for pulmonary administration by oral or nasal inhalation, and which comprises droplets of an aqueous solution of disodium cromoglycate. The aerosol is further characterized in that it has a fine particle fraction of at least about 30%. Again, the fine particle fraction may be defined as the percentage by weight of aerosol droplets having a diameter of less than about 5 µm, and more particularly, less than about 3.3 µm.

With respect to the individual features of the nebulized aerosol, reference is made to the respective explanations in the context of the method of treatment described above. Moreover, the nebulized aerosol can be prepared by providing a volume of an aqueous composition comprising disodium cromoglycate in dissolved form, providing a nebulizer capable of nebulizing said composition into an aerosol exhibiting a fine particle fraction of at least about 30%, and nebulizing said volume by said nebulizer into an aerosol. The same preferences apply for the nebulized aerosol and its preparation as have been disclosed for the method of treatment.

In particular, a nebulizer may be selected which is capable of generating an aerosol comprising a fine particle fraction of at least about 40%. Moreover, the mass median aerodynamic diameter may be less than about 4 µm, and its geometric standard deviation may be less than about 2.3. While such nebulizer aerosol may be generated with a carefully selected nebulizer from the group of jet nebulizers, ultrasonic nebulizers, vibrating membrane nebulizers, and electronic nebulizers, the most preferred nebulizers are high-performance jet nebulizers and electronic or perforated vibrating membrane nebulizers which meet the criteria defined herein.

In a further aspect, the invention provides the use of a nebulizer exhibiting a small residual volume for nebulizing an aqueous composition comprising from about 1 to about 5 wt-% disodium cromoglycate in dissolved form. The nebulized aerosol exhibits a fine particle fraction—as defined above—of at least about 30%. Specifically, the nebulizer is an electronic vibrating membrane nebulizer. In particular, a nebulizer may be selected which exhibits a residual volume of less than about 1 ml, or less than about 0.5 ml, or less than about 0.3 ml, and in particular of less than about 0.2 ml. Again, for the individual features associated with this use, reference is made to the disclosure of the same features and related preferences in the context of the method of treatment herein above.

In a further aspect, the invention provides the use of a nebulizer delivering a respirable dose of at least 2 mg contained in droplets less than about 3.3 µm, which has a high probability to be deposited into the distal airways. It is known from pharmacokinetics, that the residence time and elimination time of a drug may be affected by the dose, too. Hence, if a very high dose can be deposited the elimination half time of a drug may be prolonged. This aspect is important when a drug should be dosed several times a day, which compromises patient's compliance. Hence, the invention is focusing on the delivery of a high fine particle dose into the lung periphery offering the chance to reduce the currently recommended dosing frequency from 4 times daily to only twice daily. However, a reduction in dosing frequency requires that the absolute lung dose obtained from a 4 times daily administration so far must be at least the same or even higher to achieve a therapeutic effect for a twice daily dosing regime. This can be either accomplished by a dose increase or the use of a very efficient nebulizer system, such as eFlow, which gives a several fold higher respirable dose less than about 3.3 µm compared to currently established drug delivery systems.

In particular, the use involves a nebulizer capable of emitting an aerosol having a mass median aerodynamic diameter which is less than about 4 µm, or having a geometric standard deviation which is preferably less than about 2.3. Moreover, the use comprises the nebulization of a volume of an aqueous composition comprising from about 10 to about 20 mg of disodium cromoglycate within a period of less than about 5 minutes. In a further embodiment, the aerosol may be administered by oral or nasal inhalation to a patient affected by a pulmonary disease or condition.

Optimal compositions and methods will vary according to factors such as the active ingredient or ingredients, amount of time the formulation will be stored, conditions under which it will be stored and used, including the dosage form of the composition, and the particular patient population to which it may be administered.

Without further elaboration, it is believed that one skilled in the art, using the preceding description, can utilize the invention to the fullest extent. The following examples for the inventive aqueous drug formulations for nebulization are illustrative only, and not limiting of the disclosure in any way whatsoever.

The following examples are merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in the cellular and molecular biology fields or related fields are intended to be within the scope of the appended claims.

The disclosures of all references and cited publications are expressly incorporated by reference in their entireties to the same extent as if each were incorporated by reference individually.

EXAMPLES

Specific Example 1

About 1 kg DSCG and about 0.9 kg sodium chloride were weighted into a mixing tank and dissolved in about 100 kg water for injection under stirring. Thereafter, the solution was filtered through about a 0.22 μm sterile filter, and aliquots of about 2 ml were filled under aseptic conditions into blow-fill-seal vials made of low density polyethylene.

Specific Example 2

About 5 kg DSCG and about 0.9 kg sodium chloride were weighed into a mixing tank and dissolved under stirring in about 100 kg water for injection, the pH was adjusted to about 6 by the addition of about 0.1 M hydrochloric acid. Thereafter, the solution was filtered through a 0.22 μm sterile filter and aliquots of about 0.5 ml were filled under aseptic conditions into blow-fill-seal vials.

Results of the physicochemical characterization of examples 1 and 2 compared to the reference product currently on the market are shown in the Table 1, immediately below.

TABLE 1

| Composition | DSCG Concentration | pH | Dynamic viscosity [mPas] | Surface Tension [mN/m] | Osmolality [mOsmol/kg] |
|---|---|---|---|---|---|
| Intal ampules | 10 mg/ml | 5.80 | 1.04 ± 0.03 | 71.57 ± 0.08 | 44 ± 1 |
| DSCG solution of example 1 | 10 mg/ml | 5.52 | 1.04 ± 0.03 | 72.60 ± 0.24 | 303 ± 0 |
| DSCG solution of example 2 | 50 mg/mL | 6.03 | 1.23 ± 0.01 | 72.11 ± 0.11 | 333.6 ± 0.0 |

Specific Example 3

About 2 kg DSCG, about 0.4 kg albuterol-sulphate and about 0.7 kg sodium chloride and about 200 g saccharin sodium were weighed into a mixing tank and dissolved under stirring in about 100 kg water for injection. After adjusting the pH to 4 by addition of about 0.1 M hydrochloric acid, the solution was filtered through a 0.22 μm sterile filter and about 1 ml were filled under aseptic conditions into blow fill seal vials.

Specific Example 4

About 2.5 kg DSCG, about 0.25 kg ipratropium bromide and about 0.7 kg sodium chloride and about 1 kg xylitol were weighed into a mixing tank and dissolved under stirring in about 100 kg water for injection. Thereafter, the solution was filtered through a 0.22 μm sterile filter and about 0.5 ml were filled under aseptic conditions into blow fill seal vials.

Specific Example 5

About 5 kg DSCG, about 0.02 kg fluticasone-propionate, about 5 kg gamma cyclodextrin and about 0.5 kg sodium chloride were weighed into a mixing tank and dissolved under stirring in about 100 kg water for injection. Thereafter, the solution was filtered through a 0.22 μm sterile filter and 0.5 ml are filled under aseptic conditions into blow fill seal vials.

Specific Example 9

About 2 kg DSCG, about 2 kg sodium hydrogencarbonate, about 0.4 kg sodium chloride were weighed into a mixing tank and dissolved under stirring in about 100 kg water for injection. Thereafter, the solution was filtered through a 0.22 µm sterile filter and about 2 ml are filled under aseptic conditions into blow fill seal vials.

Specific Example 10

About 5 kg DSCG, about 5 kg gamma cyclodextrin, about 0.25 kg theophyllin, about 0.1 kg gamma tocopherol-acetate and about 0.5 kg sodium chloride were weighed into a mixing tank and dissolved under stirring in about 100 kg water for injection. Thereafter, the solution was filtered through a 0.22 µm sterile filter and about 0.5 ml is filled under aseptic conditions into 1 ml blow fill seal vials.

Specific Example 11

About 1 kg DSCG, about 2 kg alpha-antitrypsin and about 0.8 kg sodium chloride were weighed into a mixing tank and dissolved in about 100 kg water for injection under stirring. Thereafter, the solution was filtered through a 0.22 µm sterile filter and filled under aseptic conditions into about 1 ml blow fill seal vials.

Specific Example 12

About 2.5 kg DSCG, about 2.5 kg levofloxacin, about 2.5 kg magnesium-chloride, 0.1 kg saccharin-sodium, 0.1 kg xylitol and about 0.5 kg sodium chloride were weighed into a mixing tank and dissolved in about 100 kg water for injection under stirring. Thereafter, the solution was filtered through a 0.22 µm sterile filter and filled under aseptic conditions into about 2 ml blow fill seal vials.

Specific Example 13

About 2 kg DSCG, about 10 g procaterol-hydrochlodride and about 0.9 kg sodium chloride were weighed into a mixing tank and dissolved under stirring in about 100 kg water for injection. The pH was adjusted to 5-6 and the solution filtered thereafter through a 0.22 µm sterile filter and 1 ml were filled under aseptic conditions into blow fill seal vials.

Specific Example 14

This example describes the experimental set-up to assess and compare the suitability and efficiency of pulmonary drug delivery systems, such as MDIs, DPIs and nebulizers for pulmonary administration of DSCG formulations. Utilizing a pMDI or Acron nebulizer (MMD=4.5 µm) to administer a dose of 20 mg DSCG, only 0.3% or 1.5%, respectively, of lung deposition was calculated based on timed urine collections.

Hence, the purpose of this example is to assess in vitro what delivery system would be most appropriate for the delivery of DSCG in humidity saturated lungs using the Next Generation Impactor (NGI) as a tool to investigate humidity effects on the delivery performance of a MDI, DPI and two other nebulizer systems suitable for use in children.

For a comparative assessment, Intal® HFA MDI (1 mg/puff), and Intal® 20 mg capsule (both from Sanofi-Aventis Pharma Deutschland GmbH, Frankfurt, Germany) were compared with IsoCROM® (20 mg/2 ml isotonic solution, PARI, Starnberg, Germany) nebulized via the breath enhanced PARI LC® SPRINT JUNIOR powered by a PARI BOY®SX compressor and an eFlow® 30S electronic nebulizer (all from PARI Starnberg Germany).

A NGI was placed in a box suitable to adjust both, the temperature and humidity of ambient and entrained air including the impactor. Aerosolization into the NGI was conducted at an atmosphere of about 50%±5% and at about 95%±5% relative humidity (RH) at a temperature of 23°±2° C. RH by means of an impinger placed in a water-bath. For the nebulizer experiments the flow rate was about 15 L/min each and the impactor temperature about 18°±2° C. for 50% RH and 23° C.±2° C. for 95% RH entrained air, respectively. For the Intal® MDI and DPI experiments at 50% and 95% RH the NGI-temperature was 23° C.±2° C., each and the flow rate 30 L/min for the MDI and 60 L/min for the DPI for 4 sec, each. 20 mg DSCG (20 puffs from the MDI, 1 capsule from the DPI or 2 ml isotonic solution) were used in each test.

The drug was quantified by a validated internal standard HPLC/UV method. Tests were carried out with 3 individual devices, each and mean values were calculated from 3 tests, each (n=3). Statistical analysis was conducted according to a one way ANOVA using STATGRAPHICS (StatPoint Inc. Dulles, Va., USA).

Figure 2:
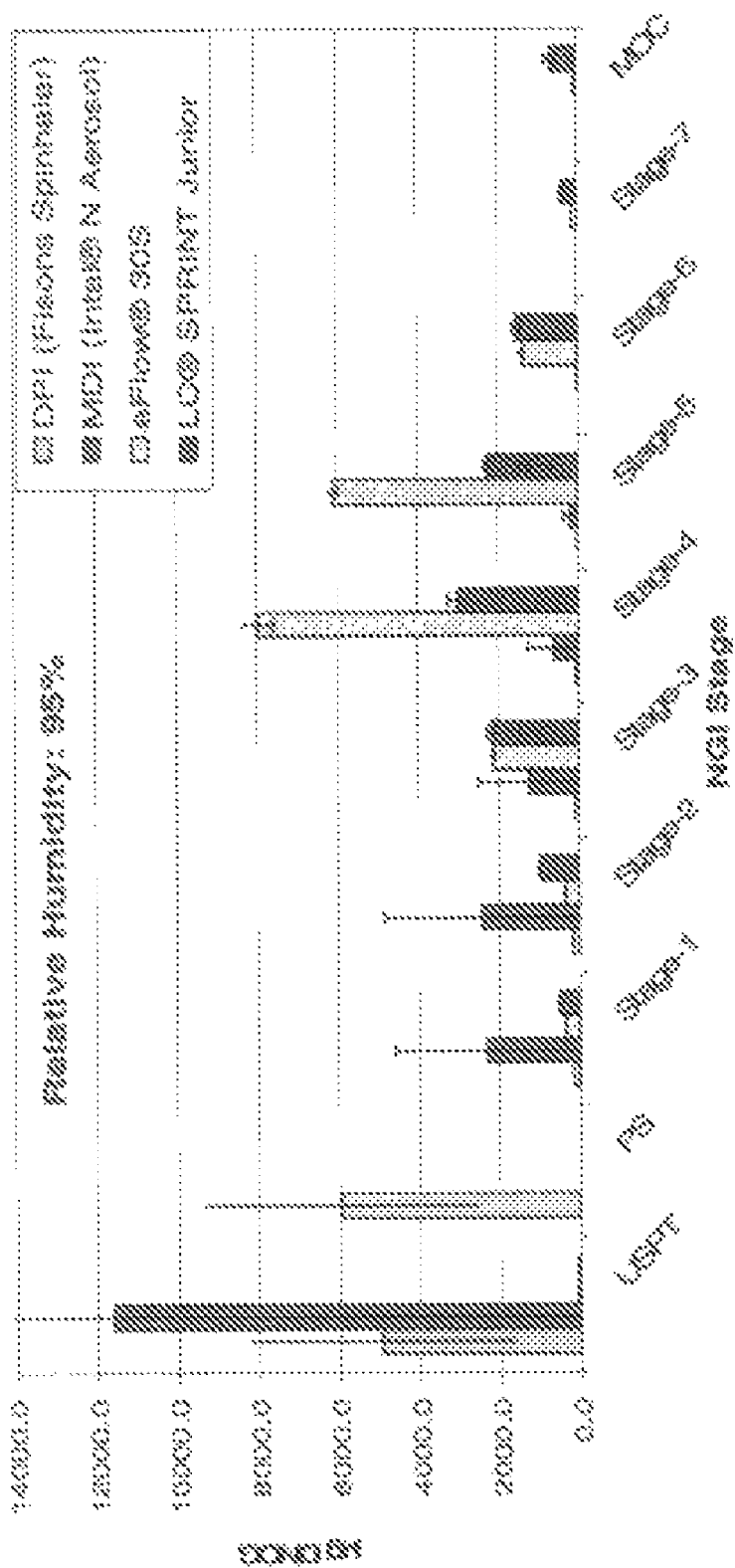
FIG. 2 shows the mean results on NGI drug distribution patterns in mg±SD obtained from about 20 mg DSCG, each aerosolized through 4 inhalation systems in triplicate, each at about 95% RH.

Data from the NGI experiments are presented in FIG. 1 (50% RH) and FIG. 2 (95% RH). It is apparent from both graphs, that results for the MDI and DPI are highly variable and most drug is found in the induction port, pre-separator, and on stages 1-3, and much less on stages 4-7 representing particles less than about 3.3 µm. 95% relative humidity is affecting the DSCG distribution pattern in an NGI and causes different significant effects on the fine particle dose (FPD) at the 95% confidence level for a MDI (p=0.0001), DPI (p=0.0043), the eFlow® 30S (p=0.0351) and the PARI LC® Sprint junior (p=0.0213). Variability of results was less for the two nebulizers and the majority of drug was found on NGI stages 4-7 representing particles less than about 3.3 µm regarded as therapeutically most important.

Results from the NGI experiments are summarized in Table 2 comparing the recommended treatment dose of 2 mg from an Intal® MDI versus 20 mg delivered either via a Fisons Spinhaler® from capsule or via two nebulizers from 2 ml isotonic DSCG solution. The FPD less than about 5 µm and 3.3 µm was at 95% RH for the PARI LC® Sprint junior up to about 80-fold and for the eFlow® 30S up to about 127-fold higher compared to the MDI and DPI indicating towards sub-therapeutic doses of the latter.

TABLE 2

| | Inhalation device | | | | | | | |
|---|---|---|---|---|---|---|---|---|
| | Intal ® MDI | | Intal ® DPI | | LC ® Sprint junior | | eFlow ® 30S | |
| Relat. humidity [%] | 50 | 95 | 50 | 95 | 50 | 95 | 50 | 95 |
| mg DSCG <5 µm | 0.33 | 0.13 | 2.5 | 0.21 | 6.7 | 7.4 | 15.6 | 14.7 |
| mg DSCG <3.3 µm | 0.14 | 0.06 | 1.6 | 0.11 | 4.4 | 4.8 | 9.4 | 7.6 |
| MMAD [µm] | 5.3 | 8.9 | 3.9 | 5.8 | 3.8 | 3.8 | 3.3 | 3.6 |
| GSD | 2.0 | 2.0 | 2.0 | 2.1 | 2.0 | 2.1 | 1.5 | 1.5 |

The data indicated that DSCG MDIs and DPIs were most probably inappropriate for drug delivery into the deep lungs due to the hygroscopicity of DSCG. Data from table 1, above, show that the amount of drug corresponding to a size below 3.3 µm required for deep lung deposition was much higher when nebulizers were used as delivery system. Most striking was the finding, that at 95% relative humidity this fraction is about 2.3-14.5 fold decreased for a pMDI and DPI when humidified conditions are applied which mimic more closely humidity saturated airways. Unfortunately, it was not recognized by authors of many clinical inhalation publications that clinical efficacy can depend on the delivery system and the physicochemical properties of a drug and/or formulation. Hence, drugs may get a poor reputation when inappropriate pulmonary delivery systems are used. In sum, for the inhalation of DSCG only nebulizers producing high respirable doses less than about 3.3 µm should be used to assure a therapeutic effective dose can reach the target cells in the lung periphery. Based on the data above it is important to know which nebulizer/compressor configurations may be most appropriate for nebulization of DSCG.

In addition to the NGI tests additional tests were conducted using the 8-stage Andersen cascade impactor (ACI), which is used most commonly in the United States. The ACI was calibrated at a continuous flow rate of about 28.3 L/min and environmental and feeding air conditions were about 23° C.±2° C. at 50%±5% relative humidity (RH). The ACI was conditioned at about 18° C.±0.5° C., as droplet evaporation has been described to be an issue with this impactor type. The drug was extracted from the USP-throat and different stages of the ACI and quantified by a validated HPLC assay.

Specific Example 15

This example compares the aerodynamic ACI droplet size distribution of the PARI LC® STAR jet nebulizer powered by a PARI BOY®N compressor versus an eFlow® 30S and eFlow® 25 S electronic nebulizer.

It is apparent from the data in Table 3, that all three nebulizers are suited for delivery of DSCG into the lungs of both adults and children, since about 42% of droplets are in a size range of 2.1-3.3 µm and the MMAD is ranging from about 3 to 3.4 µm. The eFlow® 25S is particularly suited for drug delivery of DSCG into the lungs of young kids, toddlers and infants, since about 60% of droplets are in a size range from about 2.1 µm to about 3.3 µm, and the corresponding MMADs is about 2.5 µm. Table 3

It must be considered in this context, that impactor or laser diffraction measurements are usually conducted at a constant air flows which do not reflect the dynamics of breathing patterns. Hence, in addition to aerosol droplet size characterization and distribution techniques, breath simulation test were conducted, as well.

Figure 3:
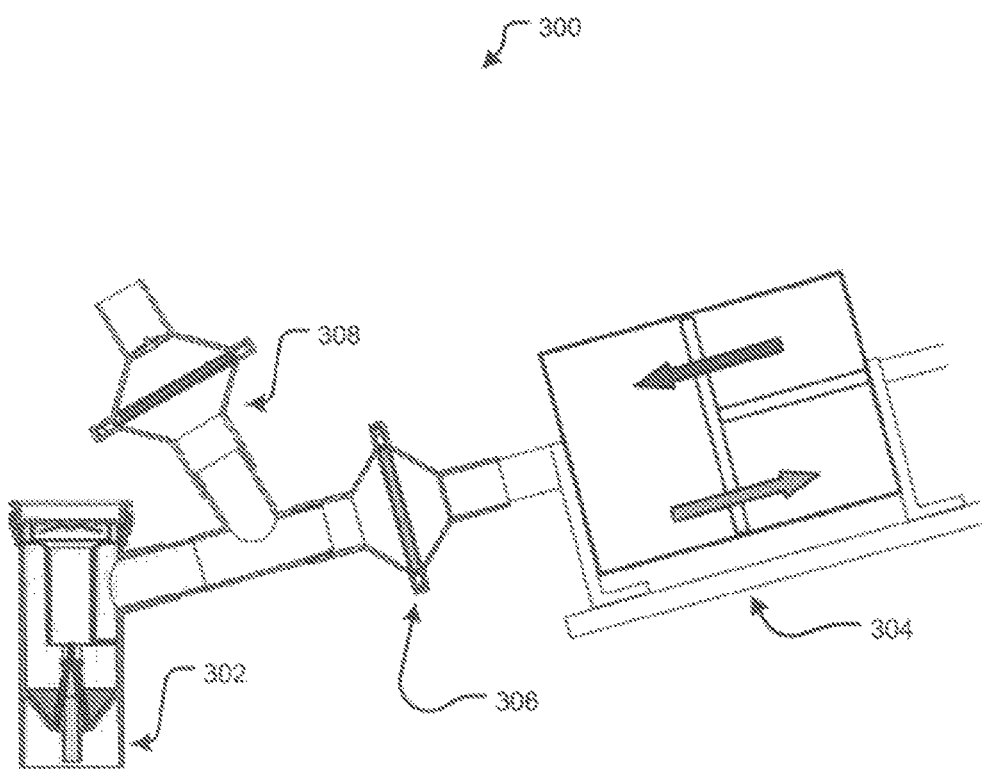
FIG. 3 shows a nebulizer system according to principles of the invention.

The efficacy of drug therapy using a nebulizer depends on both, the efficiency of the nebulizer system consisting of the nebulizer and the driving gas flow being in most cases generated by a compressor. The jet flow of the compressor will affect both droplet size and output rate. Another parameter affecting the delivery efficiency of a nebulizer configuration is the breathing maneuver of a patient. During the treatment, which can last over several minutes, the patient breathes tidally in and out of a nebulizer. Drug uptake only occurs during the inhalation phase of the breathing cycle. Any drug which is aerosolized during the exhalation phase of the patients breathing cycle is potentially lost to the environment. Hence, information on the effect of breathing pattern on the total amount of drug which is exiting the mouthpiece (=delivered dose, DD) and potentially reaching the patient's lungs (=respirable dose, RD) may be important to rate and compare the efficiency of a nebulizer system. A breath simulator test set-up which can be used to study the delivered dose of a nebulizer dependent on a breathing pattern is shown in FIG. 3. Referring to FIG. 3, a nebulizing system 300, a pump system 302 for generating a breathing pattern, an inhalation filter 304 for dose collection, and an exhalation filter 306 for collection of aerosol losses is shown.

Since both, the specific drug/nebulizer configuration and breathing pattern (inspiratory flow rate, inhalation/exhalation ratio, tidal volume, breathing frequency) can affect nebulization performance (delivered dose, treatment time), in-vitro tests mimicking different breathing patterns will provide valuable information on drug delivery characteristics.

The examples illustrated immediately below show the effect of the nebulizer type and breathing on the drug delivery efficiency of jet nebulizers, such as the PARI LC® PLUS or Hudson MicroMist® compared to the electronic nebulizer eFlow®30S developed for drug delivery of children either via an oral or face mask inhalation and eFlow®25S for aerosol delivery of infants via a face mask. In each case about 2 ml of an aqueous isotonic DSCG solution (prepared according to example 1) was nebulized for better comparison. Breath simulation experiments were performed using a COMPAS™ breathing simulator (PARI GmbH, Starnberg, Germany).

|  | Nebulizer Type | | | | | |
| --- | --- | --- | --- | --- | --- | --- |
|  | PARI LC ® STAR | | eFlow ® 30S | | eFlow ® 25S | |
| Stage Deposition [%] | Mean | SD | Mean | SD | Mean | SD |
| USP-Throat | 1.07 | 0.09 | 0.27 | 0.08 | 0.11 | 0.03 |
| stage 0 (<10.00 µm) | 2.17 | 0.25 | 0.81 | 0.12 | 0.37 | 0.10 |
| stage 1 (<9.00 µm) | 5.94 | 0.49 | 3.10 | 0.66 | 0.96 | 0.36 |
| stage 2 (<5.80 µm) | 10.63 | 0.75 | 9.36 | 1.73 | 2.98 | 1.17 |
| stage 3 (<4.70 µm) | 25.17 | 1.01 | 40.43 | 1.53 | 24.83 | 6.62 |
| stage 4 (<3.30 µm) | 24.79 | 0.65 | 29.92 | 1.32 | 36.07 | 2.41 |
| stage 5 (<2.10 µm) | 17.16 | 0.71 | 12.16 | 1.62 | 24.37 | 5.52 |
| stage 6 (<1.10 µm) | 3.57 | 0.17 | 2.06 | 0.44 | 6.60 | 3.35 |
| stage 7 (<0.65 µm) | 1.90 | 0.38 | 1.33 | 0.14 | 2.88 | 1.37 |
| Filter stage (<0.43 µm) | 7.61 | 0.67 | 0.55 | 0.05 | 0.83 | 0.19 |
| MMAD [µm] | 3.01 | 0.12 | 3.41 | 0.10 | 2.54 | 0.30 |
| GSD | 1.36 |  | 1.51 |  | 1.73 |  |
| % FPF of Stages 4 + 5 | 41.95 | 1.36 | 42.08 | 2.94 | 60.44 | 7.93 |

DSCG collected on the inhalation filter was recovered and analyzed by a validated HPLC method and UV detection to quantify the delivered dose. In addition to a standardized breathing pattern, low volume pattern, representative for child's of different age groups, was also investigated While breath simulation experiments allow the in-vitro assessment of the dose which the patient receives from the nebulizer, the geometric droplet size distribution can be determined by laser diffraction and the aerodynamic droplet size distribution by cascade impaction, as shown and described previously in the experimental setup, in FIG. 3.

Specific Example 16

An electronic nebulizer, eFlow® 30S, and four jet nebulizers, the Hudson RCI Micro Mist® powered by a PulmoAide® compressor (DeVilbis, USA) and the PARI LC® STAR, the LC® SPRINT JUNIOR and the LC® SPRINT STAR powered by a PARI BOY® N compressor (=PRONEB Ultra, USA), each (PARI Starnberg Germany), were tested for their capability to aerosolize a DSCG solution efficiently. The breath enhanced jet nebulizers from the SPRINT family, the junior (yellow nozzle insert=30) and the LC® SPRINT STAR (red nozzle insert=25) generated different droplet sizes and were designed for use in pre-school children, toddlers and infants.

The DSCG solution prepared according to example 1 was nebulized. Droplet size distribution patterns were assessed upon nebulization of 2 ml, each by laser diffraction utilizing a Malvern MasterSizer X (Malvern, Herrenberg Germany) at an entrained air flow of 20 L/min and 22±2° C. and 55±5% RH. The corresponding mass median diameter (MMD), geometric standard deviation (GSD) and respirable fractions (RF) less than about 5 and less than about 3.3 µm were calculated using the Malvern software version 2.15. The delivered dose (DD) was assessed using the PARI COMPAS™ breath simulator mimicking different breathing patterns representative for adults, children and infants. The respirable dose (RD) was calculated as follows: mg DD×% RF/100.

Figure 4:
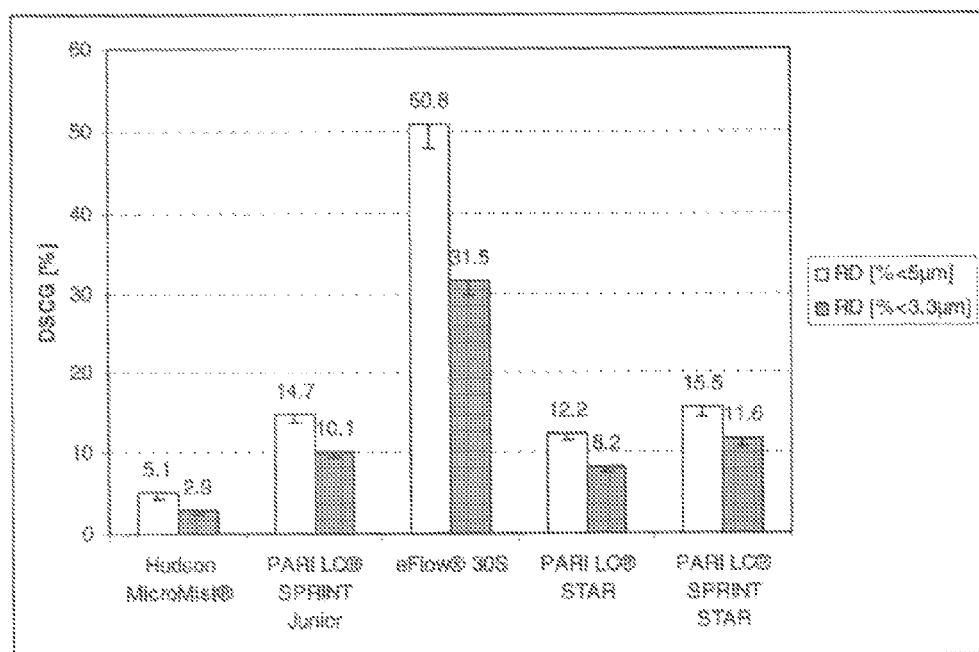
FIG. 4 shows the effect of the nebulizer type on the respirable DSCG dose (RD), according to principles of the invention.

The effect of the nebulizer type on the respirable DSCG dose (RD) is shown in FIG. 4. A T-piece type nebulizer, such as the Hudson Micro Mist® was comparable to a nebulizer type used for the clinical assessment of DSCG. Compared to the Hudson MicroMist® the percentage of small droplets less than about 3.3 µm being regarded necessary for a therapeutic effect due to deep lung deposition is about 2.8 to 4-fold higher for the breath enhanced PARI jet nebulizers and about 10-fold higher for eFlow® 30S. It may be concluded, that the Hudson MicroMist® will deliver substantially less drug into the deep lungs compared to the other nebulizer tested.

Data obtained from different nebulizer types applying 2 different breathing patterns representative for an adult (15 breaths, tidal volume 500 ml, inh:exh=50:50) and a 3 year old child (24 breaths, TV=125 ml, inh:exh=40:60) are displayed in Table 3, immediately below. From additional droplet size parameters assessed by laser diffraction (LD) tests, corresponding respirable doses (RD) and respirable drug delivery rates (RDDR) were calculated. There was no obvious difference regarding DD, RD, RDDR and nebulization times are apparent for the PARI LC® STAR and LC® SPRINT STAR.

TABLE 4

| | Nebulizer | | | | | |
|---|---|---|---|---|---|---|
| Compressor | PARI LC STAR PARI Boy N | | PARI LC SPRINT STAR PARI Boy N | | eFlow 30S n/a | |
| Breathing pattern | Adult | 3 years | Adult | 3 years | Adult | 3 years |
| MMD (µm) | 3.1 | 3.7 | 2.8 | 2.7 | 3.2 | 3.2 |
| GSD | 2.0 | 2.3 | 2.3 | 2.4 | 1.5 | 1.5 |
| Droplet fraction <5 µm (%) | 78.8 | 65.2 | 81.5 | 82.1 | 84.7 | 85.1 |
| Droplet fraction <3.3 µm (%) | 54.2 | 43.5 | 59.3 | 61.4 | 52.6 | 52.8 |
| Delivered dose (%) | 29.4 | 18.7 | 32.6 | 18.9 | 64.3 | 59.7 |
| Dose in fraction <5 µm (%) | 23.2 | 12.2 | 26.6 | 15.5 | 54.5 | 50.8 |
| Dose in fraction <3.3 µm (%) | 15.9 | 8.2 | 19.3 | 11.6 | 33.8 | 31.5 |
| RDDR <5 µm (%/min) | 5.1 | 2.1 | 6.8 | 3.0 | 14.2 | 13.2 |
| RDDR <3.3 µm (%/min) | 3.5 | 1.4 | 4.9 | 2.3 | 8.8 | 8.2 |
| Nebulization time (min) | 4.7 | 5.8 | 4.0 | 5.2 | 3.9 | 3.9 |

From data in Table 4 above, it may be concluded that delivery efficiency of eFlow® 30S was only slightly affected when different breathing patterns were applied. This feature qualifies eFlow® to be superior over jet nebulizers.

Novel DSCG formulations were prepared as shown in the table 5 below. The concentration is given as weight/weight (w/w) for drug and excipients, respectively.

TABLE 5

| | DSCG | | | |
|---|---|---|---|---|
| | 2% (w/w) | 3% (w/w) | 4% (w/W) | 5% (w/w) |
| Sodium chloride | 0.7% | 0.7% | 0.7% | 0.7% |
| Xylitol | 0.5% | 0.5% | 0.5% | 0.5% |
| Water for injection ad | 100% | 100% | 100% | 100% |

The corresponding amount of DSCG and excipients to produce 1 kg of product were weighted into a stirring vessel, each and dissolved in water for injection under stirring for 15 min, each. The pH was adjusted to 7 by the dropwise addition of either 0.1N sodium-hydroxide or 0.1N hydrochloric-acid solutions. After stirring for another 5 min, the solution was sterile-filtered under aseptic conditions in a laminar airflow hood and about 2 ml of each solution were filled in the laminar air-flow hood under aseptic conditions into pre-sterilized vials. Breath simulation tests mimicking an adult (15 breaths, tidal volume 500 ml, inh:exh=50:50) and 3 year old children breathing pattern (24 breaths, TV=125 ml, inh:exh=40:60) were conducted for the assessment of the delivered dose (DD). In parallel, laser diffraction tests were performed to obtain information on the droplet size distribution pattern as described elsewhere. The respirable dose (RD) contained in droplets less than about 3.3 μm was calculated as follows: % DD×% droplets less than about 3.3 μm. Results as follows were obtained and shown in FIG. 5.

It is apparent from data shown in FIG. 5, that eFlow® 30 S performs similar over a wide range of DSCG concentrations and nominal doses and is independent from the breathing pattern applied. The drug in droplets less than about 3.3 μm is even for the lowest dose tested greater than about 3 mg supporting the view that due to the much higher respirable doses obtained from current delivery systems less frequent dosing may be sufficient to obtain a similar or even better therapeutic effect and patient compliance.

The examples given above are merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in the pharmaceutical sciences or related fields are intended to be within the scope of the appended claims.

The disclosures of all references and publications cited above are expressly incorporated by reference in their entireties to the same extent as if each were incorporated by reference individually.

What is claimed is:

1. A method for treating a patient afflicted with a pulmonary disease or condition selected from the group consisting of chronic obstructive pulmonary disease, allergic asthma, non-allergic asthma, wheezing, and any other inflammatory or allergic lung diseases, said method comprising the steps of:
providing a volume of a pharmaceutically acceptable aqueous composition including disodium cromoglycate in dissolved form at a concentration of greater than 2 wt.-%;
nebulizing the volume by a nebulizer into an aerosol, wherein the aerosol exhibits a fine particle fraction of at least 30% of droplets having a size less than 3.3 μm, and wherein the difference between the mass median aerodynamic diameter when measured at room temperature and at a relative humidity of about 50% and the mass median aerodynamic diameter when measured at room temperature and at a relative humidity of about 95% is less than 0.5 μm; and
delivering said aerosol to the patient;
wherein the fine particle fraction is defined as the percentage of aerosol droplets having a diameter of less than 3.3 μm.

2. The method of claim 1, wherein the aerosol is adapted for pulmonary or nasal administration by oral or nasal inhalation or application.

3. The method of claim 1, wherein the volume of the aqueous composition is in the range from about 0.4 to about 2 ml.

4. The method of claim 1, wherein the amount of disodium cromoglycate in the pharmaceutically acceptable aqueous composition is in the range of about 5 mg to about 50 mg.

5. The method of claim 1, wherein the amount of disodium cromoglycate in the pharmaceutically acceptable aqueous composition is in the range of about 10 mg to about 60 mg.

6. The method of claim 1, wherein the concentration of the dissolved disodium cromoglycate in the aqueous composition is in the range of about 2 wt.-% to about 5 wt.-%.

7. The method of claim 1, wherein the aqueous composition exhibits an osmotic pressure of at least 200 mOsmol/kg.

8. The method of claim 1, wherein the aqueous composition exhibits a dynamic viscosity in the range of about 1 mPas to about 2 mPas.

9. The method of claim 8, wherein the dynamic viscosity is in the range of about 1 mPas to about 1.4 mPas.

10. The method of claim 1, wherein the aqueous composition exhibits a surface tension in the range of about 50 mN/m to about 75 mN/m.

11. The method of claim 1, wherein the nebulizer in said nebulizing step is capable of nebulizing the aqueous composition into an aerosol exhibiting a fine particle fraction of at least 30% in droplets having a size less than 3.3 μm and wherein greater than 20 wt.-% of the nominal drug dose is contained in droplets having a size in the range of about 2 μm to about 4 μm.

12. The method of claim 1, wherein the nebulizer in said nebulizing step is capable of nebulizing the aqueous composition into an aerosol such that the droplets exhibit a mass median aerodynamic diameter of less than 4 μm.

13. The method of claim 1, wherein the nebulizer in said nebulizing step is capable of nebulizing the aqueous composition into an aerosol such that the droplets exhibit a mass median aerodynamic diameter having a geometric standard deviation of less than 2.3.

14. The method of claim 13, wherein the mass median aerodynamic diameter has a geometric standard deviation of less than 2.

15. The method of claim 1, wherein the nebulizer in said nebulizing step is capable of emitting at least 40 wt.-% of the volume of the aqueous composition in aerosol form.

16. The method of claim 1, wherein the nebulizer in said nebulizing step exhibits a residual volume of less than 0.2 ml.

17. The method of claim 1, wherein the nebulizer in said nebulizing step is capable of nebulizing the volume of the aqueous composition in less than 5 minutes.

18. The method of claim 1, wherein the nebulizer in said nebulizing step is selected from the group consisting of a jet nebulizer, an ultrasonic nebulizer, a vibrating membrane nebulizer, and an electronic nebulizer.

19. The method of claim 1, wherein the patient is a pediatric patient.

20. The method of claim 1, further comprising the step of administrating an effective amount of an additional active compound.

21. The method of claim 20, wherein the additional active compound drug is included in the aqueous composition.

22. A pharmaceutically acceptable nebulized aerosol adapted for pulmonary administration by oral or nasal inhalation or administration, said aerosol comprising droplets of an aqueous solution of disodium cromoglycate, such that the aerosol has a fine particle fraction of at least 30% in droplets having a size less than 3.3 μm, wherein the fine particle fraction is defined as the percentage of aerosol droplets having a diameter of less than 3.3 μm, wherein the difference between the mass median aerodynamic diameter when measured at room temperature and at a relative humidity of about 50% and the mass median aerodynamic diameter when measured at room temperature and at a relative humidity of about 95% is less than 0.5 μm, and wherein the concentration of the disodium cromoglycate in the solution is in the range of about 2 wt.-% to about 5 wt.-%.

23. The aerosol of claim 22, wherein at least 40% of the aerosol droplets have a diameter less than 4 µm.

24. The aerosol of claim 22, wherein the fine particle fraction is at least 30% in droplets having a size less than 3.3 µm.

25. The aerosol of claim 22, wherein the droplets exhibit a mass median aerodynamic diameter of less than 4 µm.

26. The aerosol of claim 22, wherein the droplets exhibit a mass median aerodynamic diameter less than 4 µm and having a geometric standard deviation of less than 2.3.

27. The aerosol of claim 26, wherein the geometric standard deviation is less than 2.

28. The aerosol of claim 22, wherein the aerosol is generated by a nebulizer selected from the group consisting of jet nebulizers, ultrasonic nebulizers, perforated and non perforated vibrating membrane nebulizers, electronic nebulizers, mechanical nebulizers, and nebulizers capable of generating an aerosol by electro-hydrodynamic, electrostatic, capillary forces, condensation, high pressure jets, or extrusion.

29. A method for reaching target cells located in deep airways of a patient afflicted with a pulmonary disease or condition selected from the group consisting of chronic obstructive pulmonary disease, allergic asthma, non-allergic asthma, wheezing, and any other inflammatory or allergic lung diseases, said method comprising the steps of:
providing a pharmaceutically acceptable composition including an effective amount of disodium cromoglycate (DSCG) in dissolved form at a concentration of greater than 2 wt.-%;
nebulizing the composition using a nebulizer to produce an aerosol exhibiting a fine particle fraction of at least 30% of droplets having a size less than 3.3 µm, wherein the difference between the mass median aerodynamic diameter when measured at room temperature and at a relative humidity of about 50% and the mass median aerodynamic diameter when measured at room temperature and at a relative humidity of about 95% is less than 0.5 µm.

30. The method of claim 29, wherein the nebulizer in said nebulizing step produces greater than 30 wt.-% of the nominal drug dose in droplets having a size less than 3.3 µm.

31. The method of claim 29, wherein the nebulizer in said nebulizing step is capable of exhibiting a high fine droplet drug output/time defined as respirable drug delivery rate for droplets having a size less than 3.3 µm.

32. The method of claim 31, wherein the respirable drug delivery rate is greater than 4% of the nominal dose disodium cromoglycate/min.

33. The method of claim 29, wherein the nebulizer in said nebulizing step uses a composition volume of less than 2 ml.

34. The method of claim 29, wherein the nebulizer in said nebulizing step uses a composition volume in the range of about 0.2 ml to about 1.5 ml.

35. The method of claim 29, wherein the disodium cromoglycate concentration is in the range of about 2 wt.-% to about 5 wt.-%.

36. The method of claim 29, wherein the nebulizer in said nebulizing step is capable of aerosolizing a nominal dose of DSCG in the range of about 5 mg to about 50 mg in less than 3 minutes having a respirable fraction less than 4 µm of greater than 40%.

37. The method of claim 29, wherein the nebulizer in said nebulizing step is capable of generating and delivering to the patient in less than 3 minutes a respirable dose of at least 2 mg in droplets having a size less than 3.3 µm and wherein more than 20 wt.-% of the effective amount of disodium cromoglycate is contained in droplets having a size in the range of about 2 µm to about 3.3 µm.

38. The method of claim 29, wherein the nebulizer in said nebulizing step is a low wastage perforated vibrating mesh nebulizer with a residual volume of less than 0.5 ml following nebulization of the filled volume.

39. The method of claim 29, wherein the aqueous composition includes at least one compound selected from the group consisting of a beta-agonist, an anticholinergic, an inhaled steroid, a vasodilating drug, and an anti-inflammatory drug.

40. The method of claim 39, wherein the beta-agonist is at least one compound selected from the group consisting of albuterol, terbutalin, procaterol, and formoterol, as a salt, isomer, ester, ether or prodrug thereof.

41. The method of claim 39, wherein the anticholinergic is at least one compound selected from the group consisting of ipratropium, oxitropium, and glycopyrrolate as a salt, ester, ether, isomer or prodrug thereof.

42. The method of claim 39, wherein the inhaled steroid is at least one compound selected from the group consisting of budesonide, ciclesonide, fluticasone, and mometasone as a salt, ester, ether, isomer, or prodrug thereof.

43. The method of claim 39, wherein the nebulizer in said nebulizing step is a nebulizer selected from the group consisting of a jet nebulizer, an ultrasonic nebulizer, a vibrating membrane nebulizer, and an electronic nebulizer.

44. The method of claim 29, wherein the nebulizer in said nebulizing step is capable of delivering a dose ex-mouthpiece deviating less than 20% from a breathing pattern and wherein the delivered dose does not fall below 50% when breathing patterns of children are applied.

45. The method of claim 29, wherein the effective amount of disodium cromoglycate is in the range of about 5 mg to about 50 mg.

46. The method of claim 45, wherein the effective amount of disodium cromoglycate is provided in a volume of less than 2 ml.

47. A method of delivering a pharmaceutically acceptable aerosolized composition to a patient, said method comprising the steps of:
providing a nebulizer such that the nebulizer exhibits a residual volume of less than 0.2 ml;
nebulizing an aqueous composition including an effective amount of dissolved disodium cromoglycate having a concentration in the range of about 2 wt.-% to about 5 wt.-% into an aerosol exhibiting a fine particle fraction of at least 30% in droplets less than 3.3 µm such that the aerosolized composition is delivered to the patient; and
wherein the fine particle dose in droplets less than 3.3 µm is at least 2 mg and wherein more than 20 wt.-% of the effective amount of disodium cromoglycate is contained in the droplets having a size in the range of about 2 µm to about 3.3 µm, and wherein the difference between the mass median aerodynamic diameter when measured at room temperature and at a relative humidity of about 50% and the mass median aerodynamic diameter when measured at room temperature and at a relative humidity of about 95% is less than 0.5 µm.

48. The method of claim 47, wherein a delivered dose is greater than 50% of a charged dose loaded into the nebulizer.

49. The method of claim 48, wherein the effective amount of disodium cromoglycate is nebulized in less than 5 minutes.

50. The method of claim 49, wherein the effective amount of disodium cromoglycate is in the range of about 5 mg to about 50 mg.

51. The method of claim 48, wherein the nebulizer in said nebulizing step is capable of delivering a dose ex-mouthpiece deviating less than 20% from breathing pattern and wherein the delivered doses do not fall below 50%, when breathing patterns of children are applied.

52. The method of claim 48, wherein the aerosol droplets exhibit a mass median aerodynamic diameter of less than 4 μm and wherein greater than 20% of the droplets have a size in the range of about 2 μm to about 3.3 um.

53. The method of claim 48, wherein the aerosol droplets exhibit a mass median diameter having a geometric standard deviation of less than 2.3.

54. The method of claim 53, wherein the aerosol droplets exhibit a mass median diameter of about 4 μm and having a geometric standard deviation of less than 2.

55. The method of claim 48, wherein the aerosol is administered by oral or nasal inhalation or administration via a continuous or breath triggered aerosol generation method to the patient.

56. The method of claim 48, wherein the patient is afflicted with a pulmonary disease or condition selected from the group consisting of chronic obstructive pulmonary disease, allergic asthma, non-allergic asthma, wheezing, and any other inflammatory or allergic lung diseases.

57. The method of claim 48, wherein the aqueous composition is administered to the patient at a dosing frequency in the range of about one time daily to about three times daily.

58. The method of claim 48, wherein the aqueous composition includes at least one compound selected from the group consisting of excipients, salts, sugar, sugar alcohols, and sweeteners.

* * * * *